(12) United States Patent
Reinke et al.

(10) Patent No.: US 11,168,214 B2
(45) Date of Patent: Nov. 9, 2021

(54) METHOD FOR IDENTIFYING THE EXTENT OF AGING IN AN ASPHALT

(71) Applicants: A.L.M. Holding Co., Onalaska, WI (US); Ergon Asphalt & Emulsions, Inc., Jackson, MS (US)

(72) Inventors: Gerald H. Reinke, La Crosse, WI (US); Gaylon L. Baumgardner, Arkadelphia, AR (US); Andrew Hanz, La Crosse, WI (US)

(73) Assignees: A.L.M. Holding Company, Onalaska, WI (US); Ergon Asphalt & Emulsions, Inc., Lackson (MS)

( * ) Notice: Subject to any disclaimer, the term of this patent is extended or adjusted under 35 U.S.C. 154(b) by 232 days.

(21) Appl. No.: 16/308,367

(22) PCT Filed: Dec. 5, 2016

(86) PCT No.: PCT/US2016/064950
§ 371 (c)(1),
(2) Date: Dec. 7, 2018

(87) PCT Pub. No.: WO2017/213692
PCT Pub. Date: Dec. 14, 2017

(65) Prior Publication Data
US 2019/0265221 A1 Aug. 29, 2019

Related U.S. Application Data

(63) Continuation-in-part of application No. PCT/US2016/037077, filed on Jun. 10, 2016.
(Continued)

(51) Int. Cl.
*G01N 33/42* (2006.01)
*C08L 95/00* (2006.01)
(Continued)

(52) U.S. Cl.
CPC .............. *C08L 95/00* (2013.01); *A61K 31/56* (2013.01); *C04B 18/16* (2013.01); *C04B 26/26* (2013.01);
(Continued)

(58) Field of Classification Search
CPC .. C08L 95/00; C08L 2555/10; C08L 2555/22; C08L 2555/60; C08L 2555/64;
(Continued)

(56) References Cited

U.S. PATENT DOCUMENTS 2,280,843 A 4/1942 Oliver et al.
2,286,244 A 6/1942 Whitacre
(Continued)

FOREIGN PATENT DOCUMENTS

GB 575484 A 2/1946
JP 2005-154465 A 6/2005
(Continued)

OTHER PUBLICATIONS

Allen, Robert; Microstructural Characterization of the Chemo-Mechanical Behavior of Asphalt in Terms of Aging and Fatigue Performance Properties, Texas A&M University, May 2013.*
(Continued)

*Primary Examiner* — Robert R Raevis
(74) *Attorney, Agent, or Firm* — Kagan Binder, PLLC

(57) ABSTRACT

Disclosed are asphalt and asphalt binders and methods for making such compositions with sterols. The sterols improve various rheological properties. Also disclosed are methods of determining the changes or improvements of various rheoloical properties.

20 Claims, 14 Drawing Sheets

Related U.S. Application Data

(60) Provisional application No. 62/385,905, filed on Sep. 9, 2016, provisional application No. 62/385,899, filed on Sep. 9, 2016.

(51) Int. Cl.

| | |
|---|---|
| *C08K 5/05* | (2006.01) |
| *A61K 31/56* | (2006.01) |
| *C04B 26/26* | (2006.01) |
| *E01C 1/00* | (2006.01) |
| *C04B 18/16* | (2006.01) |
| *G01Q 60/24* | (2010.01) |
| *E01C 7/18* | (2006.01) |

(52) U.S. Cl.
CPC ............... *C08K 5/05* (2013.01); *E01C 1/00* (2013.01); *G01N 33/42* (2013.01); *C08K 2201/00* (2013.01); *C08L 2555/10* (2013.01); *C08L 2555/22* (2013.01); *C08L 2555/60* (2013.01); *C08L 2555/64* (2013.01); *E01C 7/18* (2013.01); *G01Q 60/24* (2013.01)

(58) Field of Classification Search
CPC ....... C08L 25/00; C08K 5/05; C08K 2201/00; C08K 9/08; G01N 33/42; A61K 31/56; C04B 26/26; C04B 18/16; E01C 1/00; E01C 7/18; G01Q 60/24
USPC ..... 73/105, 866; 106/10, 31.91, 38.25, 38.8, 106/622, 668, 123.12, 124.83, 133.1, 15, 106/7.1, 164.12, 164.6, 169.54, 170.56, 106/196.1, 205.8, 216.1, 2, 17.8, 225, 106/229, 232, 246, 269, 273.1, 502, 823; 250/306, 307
See application file for complete search history.

(56) References Cited

U.S. PATENT DOCUMENTS

| | | | |
|---|---|---|---|
| 2,392,863 A | 1/1946 | Rudd | |
| 2,411,634 A | 11/1946 | Pearson | |
| 2,585,336 A | 2/1952 | McCoy | |
| 2,715,638 A | 8/1955 | Albrecht et al. | |
| 2,793,138 A | 5/1957 | Wilkinson | |
| 2,860,067 A | 11/1958 | Crews et al. | |
| 3,032,507 A | 5/1962 | Wright | |
| 3,691,211 A | 9/1972 | Julian | |
| 3,926,936 A | 12/1975 | Lehtinen | |
| 3,951,676 A | 4/1976 | Elste, Jr. | |
| 4,044,031 A | 8/1977 | Johansson et al. | |
| 4,874,432 A | 10/1989 | Kriech et al. | |
| 5,437,717 A | 8/1995 | Doyle et al. | |
| 5,473,000 A | 12/1995 | Pinomaa | |
| 5,496,400 A | 3/1996 | Doyle et al. | |
| 6,057,462 A | 5/2000 | Robinson et al. | |
| 6,770,127 B2 | 8/2004 | Kriech et al. | |
| 6,987,207 B1 | 1/2006 | Ronyak | |
| 7,448,825 B2 | 11/2008 | Kasahara et al. | |
| 7,575,767 B2 | 8/2009 | May et al. | |
| 7,811,372 B2 | 10/2010 | Nigen-Chaidron et al. | |
| 8,513,338 B2 | 8/2013 | Rodrigues | |
| 8,696,806 B2 | 4/2014 | Williams et al. | |
| 8,741,052 B2 | 6/2014 | Naidoo et al. | |
| 9,481,794 B2 | 11/2016 | Cox | |
| 9,994,485 B2 | 6/2018 | Warner et al. | |
| 10,030,145 B2 | 7/2018 | Severance et al. | |
| 10,077,356 B2 | 9/2018 | Fini | |
| 10,167,390 B2 | 1/2019 | Cox | |
| 10,669,202 B2 | 6/2020 | Reinke et al. | |
| 10,793,720 B2 | 10/2020 | Puchalski et al. | |
| 2003/0087789 A1 | 5/2003 | Scheffler | |
| 2003/0144536 A1 | 7/2003 | Sonnier et al. | |
| 2007/0122235 A1* | 5/2007 | Kasahara | E01C 23/065 404/75 |
| 2007/0151480 A1 | 7/2007 | Bloom et al. | |
| 2010/0170417 A1 | 7/2010 | Naidoo et al. | |
| 2010/0305342 A1 | 12/2010 | Wong et al. | |
| 2010/0319577 A1 | 12/2010 | Naidoo et al. | |
| 2012/0060722 A1 | 3/2012 | Montpeyroux et al. | |
| 2014/0234027 A1 | 8/2014 | Morris | |
| 2014/0338565 A1 | 11/2014 | Severance et al. | |
| 2015/0087753 A1 | 3/2015 | Koleas et al. | |
| 2015/0329702 A1 | 11/2015 | Hwang et al. | |
| 2016/0122507 A1 | 5/2016 | Cox | |
| 2016/0160453 A1 | 6/2016 | Donelson | |
| 2016/0362338 A1 | 12/2016 | Reinke et al. | |
| 2017/0370899 A1* | 12/2017 | Porot | G01N 33/42 |
| 2018/0171146 A1* | 6/2018 | Allen | G01N 33/42 |
| 2018/0209102 A1 | 7/2018 | Baumgardner et al. | |
| 2018/0215919 A1 | 8/2018 | Reinke et al. | |
| 2019/0152850 A1 | 5/2019 | Warner et al. | |
| 2019/0153229 A1 | 5/2019 | Reinke et al. | |
| 2019/0265221 A1 | 8/2019 | Reinke et al. | |
| 2020/0207944 A1 | 7/2020 | Reinke et al. | |
| 2020/0277497 A1 | 9/2020 | Reinke et al. | |

FOREIGN PATENT DOCUMENTS

| | | |
|---|---|---|
| JP | 2012-093108 A | 5/2012 |
| WO | 2004/016336 A1 | 2/2004 |
| WO | 2010/110651 A1 | 9/2010 |
| WO | 2013/090283 A1 | 6/2013 |
| WO | 2013/163463 A1 | 10/2013 |
| WO | 2017/027096 A2 | 2/2017 |
| WO | 2017/213692 A1 | 12/2017 |
| WO | 2017/213693 A1 | 12/2017 |

OTHER PUBLICATIONS

Anonymous: "Standard Test Method for Determining the Flexural Creep Stiffness of Asphalt Binder Using the Bending Beam Rheometer (BBR); ASTM D 6648-01", Aug. 1, 2001, pp. 1-14, Retrieved from the Internet: URL: ftp://185.72.26.245/Astm/1/Section04/ASTM0403/PDF/D6648.pdf, retrived on Mar. 14, 2017.

Changping Sui et al., "New Technique for Measuring Low-Temperature Properties of Asphalt Binders with Small Amounts of Material", Transportation Research Record, Transportation Research Board, Washington, DC, US, vol. 2179, Dec. 1, 2010, pp. 23-28.

G.M. Rowe, "[Delta]Tc—Some Thoughts on the Historical Development," Binder ETG Meeting, Apr. 28, 2016, pp. 1-43, retrieved from the Internet: URL:https://www.asphaltpavement.org/PDFs/Engineering_ETGs/Binder_201604/13Rowe-DTc- Historical development.pdf [retrived on Mar. 22, 2017].

Amy Epps Martin et al, The Effects of Recycling Agents on Asphalt Mixtures with High RAS and RAP Binder Ratios (Project N 9-58), Mar. 1, 2015, Retrieved from the Internet: URL:http://onlinepubs.trb.org/onlinepubs/nchrp/docs/HNCHP09-58_Phl_InterimReport.pdf [retrieved on Mar. 20, 2017].

Gerald Reinke et al., "Further Investigations Into the Impact of REOB & Paraffinic Oils on the Performance of Bitiminous Mixtures", Binder ETG Meeting, Apr. 9, 2015, pp. 1-92, Fall River, MA, USA, Retrieved from the Internet: URL:http://www.asphaltinstitute.org/wo-content/uploads/2015-April-Binder-ETG-04_Reinke_MTE-REOB-OTHER-PARAFFINIC-OILS-w-notes-w-crack-maps.pdf.

Geoffrey M. Rowe, "Asphalt Modification", 56th Illinois Bituminous Paving Conference, Dec. 15, 2015, pp. 1-42, Champaign, Illinois, USA, Retrieved from the Internet: URL:http://conferences.ict.illinois.edu/bituminousconference/56th Annual Presentations and Attendees/Rowe.pdf [retrieved on Mar. 20, 2017].

Anonymous, "The Use of REOB/VTAE in Asphalt (IS-235)," Apr. 13, 2016, pp. 1-92, Retrieved from the Internet: URL:http://www.asphaltinstitute.org/wp-content/uploads/IS235_REOB_VTAE_Asphaltinstitute.pdf [retrieved on Mar. 20, 2017].

B. Holmbom et al., "Compostion of Tall Oil Pitch", Journal of the American Oil Chemist's Society, vol. 55, Feb. 23, 1978, pp. 342-344, Retrieved from the Internet: URL:http:www.springerlink.com/content/j37742625p63ggtl/fulltext.pdf [retrieved on Apr. 24, 2012].

(56) References Cited

OTHER PUBLICATIONS

T. Verleyen et al., "Analysis of Free and Esterified Sterols in Vegetable Oils", Journal of the American Oil Chemists Society (Jaocs), vol. 79, No. 2, Feb. 1, 2002, pp. 117-122.

Hajime Takano et al., "Chemical and Biochemical Analysis Using Scanning Force Microscopy", Chemical Reviews, vol. 99, No. 10, Oct. 1, 1999, pp. 2845-2890.

R. M. Overney et al., "Friction Measurement on Phase-Separated Thin Films with a Modified Atomic Force Microscope", Nature, Nature Publishing Group, United Kingdom, vol. 359, Sep. 10, 1992, pp. 133-135.

Rubab et a., (2011) "Effects of Engine Oil Residues on Asphalt Cement Quality", Canadian Technical Asphalt Association Conference, 12 pages.

"B-Sitosterol from Soybeans" downloaded from http://www.mpbio.com/product.php?pid=02102886, downloaded on May 21, 2015, 2 pages.

"Digging Into Asphaltenes", Sep. 21, 2009, vol. 87, No. 38, 7 pages, downloaded from http://pubs.acs.org/cen/coverstory/87/8738cover.html, downloaded on Jun. 5, 2011.

T. Verleyen et al., "Influence of the Vegetable Oil Refining Process on Free and Esterified Sterols. J Am Oil Chem Soc", Article in Journal of the American Oil Chemists' Society, Sep. 2002, 8 pages.

Material Safety Data Sheet, Catalog No. 102886, Revision date: Apr. 26, 2006, Product Name: beta-Sitosterol Practical Grade, 5 pages.

B-Sitosterol.Powder, Supplier: MP Biomedicals, Printed from VWR Website, Date: Jun. 9, 2016, 1 page.

International Search Report and Written Opinion for International Application No. PCT/US2016/064950, dated Apr. 19, 2017, 12 pages.

Richard Cantrill, Ph.D., "Phytosterols and Their Esters", 2008, 13 pages.

International Search Report and Written Opinion for International Application No. PCT/US2016/037077, dated Apr. 5, 2017, 20 pages.

International Search Report and Written Opinion for International Application No. PCT/US2016/064961, dated Apr. 5, 2017, 23 pages.

Andrew Hanz et al., "Extended Aging of RAS Mixes with Rejuvenator", Aug. 10, 2016, Binder Expert task Group Meeting, retrieved from the Internet: URL:https:/lwww.asphaltpavement.org/PDFs/Engineering_ETGs/Binder201609/06 Hanz Extended Aging of RAS Mixes with Rejuvenator.pdf, retrieved on Nov. 23, 2017.

Gerald Reinke et al., "Extended Aging of RAS Mixes with Rejuvenator an Update", May 4, 2017, Binder Expert task Group Meeting, retrieved from the Internet: URL:https://www.asphaltpavement.org/PDFs/Engineering_ETGs/Binder201705/12_Reinke&Hanz_UpdateExtendedAgingofRAS.pdf, retrieved on Nov. 23, 2017.

Product Data Sheet from MP Biomedicals Website, Catalog No. 102886, beta-Sitosterol, 2015, 1 page.

Wood Chemistry PSE 406/Chem E 470, Lecture 13, Diterpenes and Triterpenes, Wood Chemistry, 2015, 5 pages.

Sui et al. (2011) "New Low-Temperature Performance-Grading Method", Transportation Research Record: Journal of the Transportation Research Board, No. 2207, pp. 43-48.

E.E. McSweeney et al., "Composition of Crude Tall Oil & Fractionation Products (Chapter 2)" in "Tall Oil and Its Uses-II", Jan. 1, 1987, Pulp Chemicals Association, pp. 12-19.

ASTM D6521-13 (2013) "Standard practice for accelerated aging of asphalt binder using a pressurized aging vessel (PAV)", ASTM International, 6 pages.

Brian Russell Cox, "Asphalt binders containing a glyceride and fatty acid mixture and methods for making and using same", U.S. Appl. No. 62/074,526, filed Nov. 3, 2014, 64 pages.

Endo (1990) "Minor components in edible fats and oils" Oil Chemistry, 39(9):611-617 {English Abstract on p. 611).

Yan et al., (2011) "Recovery of phytosterols from waste residue of soybean oil deodorizer distillate", Soybear Applications and Technology, 13 pages.

Fini et al., (2010) "Characterization and application of manure-based bio-binder in asphalt industry", Transportation Research Board 89th Annual Meeting, 14 pages.

Fini et al., (2011) "Chemical characterization of biobinder from swine manure: sustainable modifier for asphalt binder" Journal of Materials in Civil Engineering, 23(11):1506-1513.

Fini et al., (2012) "Application of swine manure in development of bio-adhesive" Allen D. Leman Swine Conference, p. 244.

Kriz et al., (2007) "Glass transition and phase stability in asphalt binders", Road Materials and Pavements Design, 30 pages.

Material Safety Data Sheet (Aug. 8, 2013) "T—SYLFAT™ DP8", Arizona Chemical Company LLC, 7 pages.

Mogawer et al., (2012) "Performance characteristics of high rap bio-modified asphalt mixtures", Transportation Research Board 91st Annual Meeting, 16 pages.

Reinke et al., (2017) "Investigation of sterol chemistry to retard the aging of asphalt binders", Transportation Research Record, 2633(1):127-135.

"SYLVAROAD™ RP 1000 performance additive", Safety Data Sheet, Arizona Chemical Company LLC, Apr. 7, 2015, 7 pages.

Tallex Pilch (Jul. 21, 2017) Ingevity Holdings SPRL, Safety Data Sheet, 12 pages.

Wakefield, Amma (Aug. 15, 2018) "ΔTc: Monitoring asphalt binder's kryptonite" Asphalt, 33(2)24-27.

Zaumanis et al., (2014) "Evaluation of different recycling agents for restoring aged asphalt binder and performance of 100 % recycled asphalt", Materials and Structures, 48(8):2475-2488.

\* cited by examiner

METHOD FOR IDENTIFYING THE EXTENT OF AGING IN AN ASPHALT

CROSS-REFERENCE TO RELATED APPLICATIONS

This application claims priority to PCT International Application No. PCT/US2016/064950, filed on Dec. 5, 2016, which claims priority to PCT International Application No. PCT/US2016/037077 filed on Jun. 10, 2016, and claims the benefit of U.S. Provisional Patent Application Nos. 62/385,905 filed Sep. 9, 2016 and 62/385,899, filed Sep. 9, 2016 each reference herein incorporated by reference in their entirety.

BACKGROUND

Asphalt pavement is one of the most recycled materials in the world, finding uses in shoulders of paved surfaces and bridge abutments, as a gravel substitute on unpaved roads, and as a replacement for virgin aggregate and binder in new asphalt pavement. Typically, use of recycled asphalt pavement is limited to sub-surface pavement layers or to controlled amounts in asphalt base and surface layers. Such uses are limited in part because asphalt deteriorates with time, loses its flexibility, becomes oxidized and brittle, and tends to crack, particularly under stress or at low temperatures. These effects are primarily due to aging of the organic components of the asphalt, e.g., the bitumen-containing binder, upon exposure to environmental factors. The aged binder is also highly viscous. Consequently, reclaimed asphalt pavement has different properties than virgin asphalt and is difficult to process.

To reduce or retard the impact of asphalt aging on the long-range performance of mixtures, numerous materials have been investigated. For example, rejuvenators are marketed with a stated goal of reversing the aging that has taken place in recycled raw materials such as reclaimed asphalt pavement (RAP) and reclaimed asphalt shingles (RAS). It is unlikely that the marketed rejuvenators actually rejuvenate asphalt and the more likely scenario is that these additives may instead serve as softening agents for the virgin binders employed in mixtures containing RAP or RAS or combinations of both. In some instances, 10% or more by weight of these softening agents are added to the virgin binder when such mixtures are produced. As a result, the entire blend of virgin binder, rejuvenating additive and recycled binder additive has reduced stiffness versus the same blend without the rejuvenating additive.

Aging can be assessed by measuring $\Delta Tc$, the difference between the Stiffness critical temperature and the creep critical temperature after aging.

SUMMARY

Disclosed are compositions and methods that may retard, reduce or otherwise overcome the effects of aging in recycled or reclaimed aged asphalt so as to preserve or retain some or all of the original properties of the virgin binder or virgin asphalt originally used when laying down the aged asphalt. In some embodiments, the disclosed compositions and methods may alter the aging rate of the total binder present in a mix containing virgin asphalt and high levels of RAP or RAS. The disclosed compositions and methods use a class of plant derived chemistry, the sterol class of compounds like those depicted in FIG. 1. While plant sterols do not contain the same number of condensed or partially unsaturated rings as asphaltenes, they do have the benefit of not being a linear or branched linear molecule.

In one embodiment, the present disclosure provides a method for identifying the extent of aging in an asphalt or binder and slowing the aging or restoring the aged asphalt or binder comprising:
  analyzing a binder for the presence or absence of surface roughness or surface defects using atomic force microscopy;
  determining the extent to which the binder is aged based on the extent to which such surface roughness or surface defects are absent; and
  adding amounts of an anti-aging additive and a virgin asphalt binder to the binder based on the extent to which such binder is determined as being aged.

In one embodiment, the present disclosure provides a method for slowing the aging or restoring aged asphalt binder comprising adding a sterol to an asphalt binder, wherein the asphalt binder comprises a virgin asphalt binder, reclaimed asphalt binder material comprising asphalt pavement (RAP), asphalt shingles (RAS) or combinations of both and from 0.5 to 15 wt. % of the sterol source based on the virgin asphalt binder In one embodiment, the present disclosure provides a method for reusing reclaimed asphalt binder for asphalt pavement production, comprising adding a sterol to an asphalt binder, wherein the asphalt binder comprises a virgin asphalt binder, reclaimed asphalt binder material comprising asphalt pavement (RAP), asphalt shingles (RAS) or combinations of both and from 0.5 to 15 wt. % of the sterol based on the virgin asphalt binder.

In another embodiment, the present disclosure provides an asphalt comprising, virgin asphalt binder, reclaimed asphalt binder material comprising reclaimed asphalt pavement (RAP), reclaimed asphalt shingles (RAS) or combinations of both, a sterol, wherein and from 0.5 to 15 wt. % of the sterol source based on the virgin asphalt binder.

In yet another embodiment, the present disclosure provides method for restoring aged asphalt binder comprising adding a sterol and virgin asphalt binder to a reclaimed asphalt binder, wherein 0.5 to 15 wt. % of the sterol is based on virgin asphalt binder.

In one embodiment, the present disclosure provides an asphalt or binder comprising virgin asphalt binder, reclaimed asphalt binder material comprising reclaimed asphalt pavement (RAP), reclaimed asphalt shingles (RAS) or combinations of both, and an anti-aging additive in the range of 0.5 to 15 wt. % of the virgin binder, wherein the anti-aging additive is free of cyclic organic compositions that contain esters or ester blends.

In one embodiment, the present disclosure provides an asphalt or binder comprising virgin asphalt binder, reclaimed asphalt binder material comprising reclaimed asphalt pavement (RAP), reclaimed asphalt shingles (RAS) or combinations of both, and a restorative additive in the range of 0.5 to 15 wt. % of the virgin binder, wherein the restorative additive is free of cyclic organic compositions that contain esters or ester blends.

In another embodiment, the present disclosure provides a method for slowing the aging or restoring aged asphalt or binder comprising:
  adding an anti-aging additive to an asphalt binder, wherein the asphalt binder comprises a binder, reclaimed asphalt binder material comprising reclaimed asphalt pavement (RAP), reclaimed asphalt shingles (RAS) or combinations of both, wherein the anti-aging additive is added in a range of 0.5 to 15 wt. % of the virgin asphalt binder.

In one embodiment, the present disclosure provides an asphalt comprising aggregate, virgin asphalt binder, reclaimed asphalt material comprising RAP, RAS or combinations of both, a triterpenoid, and a softening agent, wherein the triterpenoid preferably is free of cyclic organic esters, and has a triterpenoid content (e.g., a sterol content) of at least about 0.5, at least about 1 wt. %, at least about 5 wt. %, up to about 8%, up about 10%, or up to about 15 wt. % based on the virgin asphalt binder weight.

In another embodiment, the present disclosure provides an asphalt comprising virgin asphalt binder, reclaimed asphalt material comprising RAP, RAS or combinations of both, a triterpenoid, and a softening agent, wherein the triterpenoid preferably is free of cyclic organic esters, and has a sterol content of at least about 0.5, at least about 1 wt. %, at least about 5 wt. %, up to about 8%, up to about 10%, or up to about 15 wt. % based on the virgin asphalt binder weight.

The triterpenoid in the disclosed embodiments for example, may be a sterol, a stanol, a plant sterol, or a plant stanol.

In other embodiments, the present disclosure provides a method for retarding oxidative aging of the asphalt binder, which method comprises adding one or more triterpenoids (e.g., a triterpenoid blend) to a binder or asphalt, wherein the terpenoid(s) preferably do not contain an ester or an ester blend, and wherein the triterpenoid content in the composition is of at least about 0.5, at least about 1 wt. %, at least about 5 wt. %, up to about 8%, up about 10%, or up to about 15 wt. % based on the virgin asphalt binder weight.

Exemplary embodiments of the present disclosure include, for example, i) asphalt binder comprising RAS at a binder replacement level 1% and greater, ii) asphalt binder comprising RAP at binder replacement levels 20% and greater, iii) asphalt binder comprising RAP and RAS used in combination at binder replacement levels of 10% and greater RAP-derived binder and binder replacement levels of 1% and greater RAS-derived binder, iv) asphalt binder comprising asphalt binder extracted and recovered from post-consumer waste shingles at binder replacement levels of 3% by weight and greater, v) asphalt binder comprising asphalt binder extracted from manufacture's waste shingles at binder replacement levels of 5% by weight and greater, vi) asphalt binder comprising oxidized asphalts meeting ASTM specification D312 for Type II, Type III, or Type IV and coating asphalt at binder replacement levels of 3% by weight and greater, vii) asphalt binder comprising extracted and recovered RAP at binder replacement levels of 10% by weight and greater, viii) asphalt binder comprising re-refined engine oil bottoms (REOB) at binder replacement levels of 1% and grater by weight, ix) asphalt binder comprising paraffinic oils at binder replacement levels of 1% and greater by weight, x) asphalt paving comprising aggregate, aggregate and RAP, aggregate and RAS, or aggregate and a combination of RAP and RAS mixed with binder containing REOB at binder replacement levels of 1% and higher by weight; xi) said asphalt pavings as enumerated in x) mixed with paraffinic oils at binder replacement levels of 1% and higher by weight. In still other embodiments, the disclosure provides a method for reusing reclaimed asphalt for asphalt pavement production, which method comprises the use of one or more triterpenoids (e.g., a triterpenoid blend) as an additive to a bituminous or asphalt mixture that preferably the additive does not contain an ester or an ester blend, and wherein the triterpenoid additive is at least about 0.5, at least about 1 wt. %, and up to about 3, up to about 10, or up to about 15 wt. % based on the virgin asphalt weight.

Other embodiments comprise a method for applying a road pavement surface, which method employs an asphalt comprising aggregate, virgin asphalt binder, reclaimed asphalt material comprising RAP, RAS or combinations of both, a triterpenoid, and a softening agent, wherein the triterpenoid preferably is free of cyclic organic esters or ester blends, and has a sterol content of at least about 0.5, at least about 1 wt. %, or up to about 15 or up to about 10 wt. % based on the virgin asphalt binder weight. In a further embodiment, the asphalt paving is prepared, mixed, applied to a base surface, and compacted.

DETAILED DESCRIPTION

Figure 1:
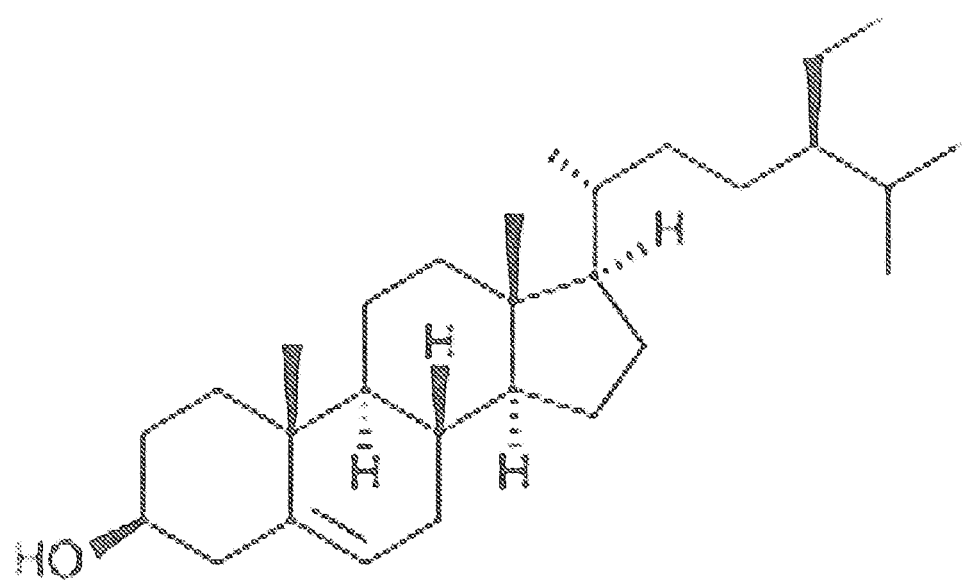
FIG. 1 depicts a representative plant sterol structure e.g., beta-sitosterol.

The disclosed asphalt contains anti-aging (viz., age reducing or aging retarding) additives that help in the preservation, recycling and reuse of asphalt or asphalt binder. The anti-aging preferably are free of cyclic organic compositions that contain esters or ester blends. The disclosed compositions have particular value for the renewal of reclaimed asphalt, and especially RAP.

The disclosed asphalt provide for recycled asphalt (e.g., RAP or RAS) the binders of which may have improved physical and rheological characteristics such as stiffness, effective temperature range, and low temperature properties compared to binders that do not contain the disclosed additives. Some embodiments provide for the use of binder extracted from RAS in asphalt blends. Certain embodiments provide for the addition of an additive to minimize potential detrimental low-temperature effects of recycled asphalt while allowing for higher stiffness at high temperatures.

Headings are provided herein solely for ease of reading and should not be interpreted as limiting.

Abbreviations, Acronyms & Definitions

"Aged" refers to asphalt or binder that is present in or is recovered from reclaimed asphalt. Aged binder has high viscosity compared with that of virgin asphalt or virgin binder as a result of aging and exposure to outdoor weather. The term "aged" also refers to virgin asphalt or virgin binder that has been aged using the laboratory aging test methods described herein (e.g. RTFO and PAV). "Aged" may also refer to hard, poor-quality, or out-of-specification virgin asphalt or virgin binder particularly virgin binders having a ring-and-ball softening point greater than 65° C. by EN 1427 and a penetration value at 25° C. by EN 1426 less than or equal to 12 dmm.

"Aggregate" and "construction aggregate" refer to particulate mineral material such as limestone, granite, trap rock, gravel, crushed gravel, sand, crushed stone, crushed rock and slag useful in paving and pavement applications.

"Anti-aging additive" refers to sterols or sterol mixes that can be combined with aged binder to retard the rate of aging of asphalt or binder, or to restore or renew the aged asphalt or aged binder to provide some or all of the original properties of virgin asphalt or virgin binder.

"Asphalt" refers to a binder and aggregate and optionally other components that are suitable for mixing with aggregate and binder. Depending on local usage, the terms "asphalt mix" or "mix" may be used interchangeably with the term "asphalt."

"Asphalt pavement" refers to compacted asphalt.

"Binder" refers to a highly viscous liquid or semi-solid form of petroleum. "Binder" can include, for example bitumen. The term "asphalt binder" is used interchangeably with the term "binder."

"Bitumen" refers to a class of black or dark-colored (solid, semisolid, or viscous) cementitious substances, natural or manufactured, composed principally of high molecular weight hydrocarbons, of which asphalts, tars, pitches, and asphaltenes are typical.

"Crude" when used with respect to a material containing a sterol means sterol that has not been fully refined and can contain components in addition to sterol.

"M-critical" or "Creep critical" grade refers to the low temperature relaxation grade of a binder. The creep critical temperature is the temperature at which the slope of the flexural creep stiffness versus creep time according to ASTM D6648 has an absolute value of 0.300. Alternatively the stiffness and creep critical temperatures can be determined from a 4 mm Dynamic Shear Rheometer (DSR) test or Bending Beam Rheometer (BBR).

"Neat" or "Virgin" binders are binders not yet used in or recycled from asphalt pavement or asphalt shingles, and can include Performance Grade binders.

PAV" refers to a Pressurized Aging Vessel. The PAV is used to simulate accelerated aging of asphalt or binder as described in ASTM D6521-13, Standard Practice for Accelerated Aging of Asphalt Binder Using a Pressurized Aging Vessel (PAV).

"Pure" when used with respect to a sterol or mixture of sterols means having at least a technical grade of purity or at least a reagent grade of purity.

"Reclaimed asphalt" and "recycled asphalt" refer to RAP, RAS, and reclaimed binder from old pavements, shingle manufacturing scrap, roofing felt, and other products or applications.

"Reclaimed asphalt pavement" and "RAP" refer to asphalt that has been removed or excavated from a previously used road or pavement or other similar structure, and processed for reuse by any of a variety of well-known methods, including milling, ripping, breaking, crushing, or pulverizing.

"Reclaimed asphalt shingles" and "RAS" refer to shingles from sources including roof tear-off, manufacture's waste asphalt shingles and post-consumer waste.

"RTFO" refers to a Rolling Thin Film Oven. The RFTO is used for simulating the short-term aging of binders as described in ASTM D2872-12e1, Standard Test Method for Effect of Heat and Air on a Moving Film of Asphalt (Rolling Thin-Film Oven Test).

"S-Critical" or "stiffness critical" grade refers to the low temperature stiffness grade of a binder. The stiffness critical temperature is the temperature at which a binder tested according to ASTM D6648 has a flexural creep stiffness value of 300 MPa or as determined by either the Bending Beam Rheometer test or 4 mm DSR test as described in ΔTc.

SHRP refers to the Strategic Highway Research Program which develops new binder specifications in 1993.

"Softening agent" refers to low viscosity additives that ease (or facilitate) the mixing and incorporation of a recycled binder into virgin binder during an asphalt production process.

"Temp" is used in Tables and Figures as a contraction for the word Temperature.

"ΔTc" refers to the value obtained when the low temperature creep or m-value critical temperature is subtracted from the low temperature stiffness critical temperature. The 4 mm dynamic shear rheometer (DSR) test and analysis procedures are described by Sui, C., Farrar, M., Tuminello, W., Turner, T., A New Technique for Measuring low-temperature Properties of Asphalt Binders with Small Amounts of Material, Transportation Research Record: No 1681, TRB 2010. See also Sui, C., Farrar, M. J., Harnsberger, P. M., Tuminello, W. H., Turner, T. F., New Low Temperature Performance Grading Method Using 4 mm Parallel Plates on a Dynamic Shear Rheometer. TRB Preprint CD, 2011, and by Farrar, M., et al, (2012), Thin Film Oxidative Aging and Low Temperature Performance Grading Using Small Plate Dynamic Shear Rheometry: An Alternative to Standard RTFO, PAV and BBr. Eurasphalt & Eurobitume 5th E&E Congress-2012 Istanbul (pp. Paper 05ee-467). Istanbul: Foundation Euraspalt.

All weights, parts and percentages are based on weight unless otherwise specified.

Binders

Current bituminous paving practices involve the use of high percentages of Reclaimed Asphalt Pavement (RAP) and Reclaimed Asphalt Shingles (RAS) as components in the bituminous mixtures being paved. Typically RAP concentrations can be as high as 50% and RAS concentrations can be as high as 6% by weight of the paving mixture. The typical bitumen content of RAP is in the range of 5-6% by weight and the typical bitumen content of RAS is in the range of 20-25% by weight. Consequently, a bituminous mixture containing 50% by weight of RAP will contain 2.5% to 3% RAP bitumen contributed to the final bituminous mixture and a bituminous mixture containing 6% RAS by weight will contain 1.2% to 1.5% RAS bitumen contributed to the final bituminous mixture. In many instances both RAP and RAS recycled additives are combined in a bituminous mixture; for example 20% to 30% RAP and 5% to 6% RAS may be incorporated into a bituminous mixture. Based on the typical bitumen contents of RAP and RAS, bituminous mixtures containing 20% to 30% RAP and 5% to 6% RAS can result in 2% to as much as 3.3% binder (based on the total mixture weight) being derived from the RAP and RAS combination. Since a typical bituminous paving mixture will contain about 5.5% total bitumen, there accordingly may be about 36% to as much as 60% of the total bitumen in the bituminous mixture from these recycled sources.

Characteristics of bitumen in these reclaimed sources relative to virgin binders used in bituminous mixtures are shown in Table 1.

the bitumen from these recycled components and retard further oxidative aging of the total bitumen in the final mixture. The last three rows of Table 2 show that the further away from the air-mixture interface, the lower the impact on $\Delta Tc$ parameter. This parameter may be used to assess the impact of aging on binder properties and more specifically the impact of aging on the relaxation properties of the binder; the relaxation property is characterized by the property referred to as "low temperature creep grade".

Research published in 2011 showed, based on recovered binder data from field cores, that $\Delta Tc$ could be used to identify when a pavement reached a point where there was a danger of non-load related mixture cracking and also when potential failure limit had been reached. In that research the authors subtracted the stiffness-critical temperature from the creep or m-critical temperature and therefore binders with poor performance properties had calculated $\Delta Tc$ values that were positive. Since 2011 industry researchers have agreed to reverse the order of subtraction and therefore when the m-critical temperature is subtracted from the stiffness critical temperature binders exhibiting poor performance properties calculate to $\Delta Tc$ values that are negative. The industry generally agreed that to have poor performing binders

TABLE 1

| Binder & source | High temperature stiffness grade, ° C. | 4 mm DSR S-critical Grade ° C., 20 hr. PAV | Critical Low temperature grade based on 4 mm DSR m-critical Grade ° C. 20 hr. PAV | $\Delta Tc$ ° C., 20 hr. PAV | Critical Low temperature grade based on 4 mm DSR S-Critical Grade ° C. 40 hr. PAV | 4 mm DSR m-critical Grade ° C. 40 hr. PAV | $\Delta Tc$ ° C., 40 hr. PAV |
|---|---|---|---|---|---|---|---|
| PG 58-28 | 60.3 | −31.4 | −30.9 | −0.5 | −30.7 | −27.8 | −2.9 |
| PG 64-22 | 67.1 | −27.1 | −26.2 | −.9 | −25.8 | −23.2 | −2.6 |

| Binder recovered from RAP or RAS | 4 mm DSR S-critical Grade | Critical Low temperature creep grade based on 4 mm DSR m-critical grade | $\Delta Tc$° C. |
|---|---|---|---|
| RAP 03-16-15-D | 85.0 | −25.5 | −22.3 | −3.2 |
| RAP 02-23-15-B | 89.5 | −25.3 | −21.3 | −4.0 |
| RAP 03-24-15-D | 98.8 | −22.4 | −17.1 | −5.3 |
| RAP 02-09-15-B | 87.5 | −27.8 | −26.2 | −1.6 |
| RAS 04-03-15-D | 158.2 | −27.5 | −0.3 | −27.2 |
| RAS 02-09-15-C | 137.7 | −25.7 | +9.7 | −35.4 |

Table 2 shows the high and low temperature properties of samples produced with virgin binders and bitumen recovered from post-consumer waste shingles after different periods of aging. Also shown in Table 2 are high and low temperature properties of mixtures containing RAP and RAS. Some of these mixtures have undergone extended laboratory aging and some are from field cores.

Tables 1 and 2 show the impact of incorporating high binder replacement levels of recycled materials, especially those derived from post-consumer waste shingles. The data demonstrate the desirability of incorporating additives into bitumen and bituminous mixtures to mitigate the impact of become more negative as performance decreased seemed to be more intuitive. Therefore, today in the industry and as used in the application, a $\Delta Tc$ warning limit value is −3° C. and a potential failure value is −5° C.

Reports at two Federal Highway Administration Expert Task Group meetings have shown a correlation between $\Delta Tc$ values of binders recovered from field test projects and severity of pavement distress related to fatigue cracking. Additionally, it has been shown that when binders used to construct these field test projects were subjected to 40 hours of PAV aging, the $\Delta Tc$ values showed a correlation to pavement distress related to fatigue cracking, especially top down fatigue cracking which is generally considered to result from loss of binder relaxation at the bituminous mixture surface.

It is therefore desirable to obtain bituminous mixtures with bitumen materials that have a reduced susceptibility to the development of excessively negative ΔTc values.

The data in Table 1 show typical virgin binders produced at refineries can maintain a ΔTc of greater than −3° C. after 40 hours of PAV aging. Further, the data in Table 1 show that binder recovered from RAP can have ΔTc values of less than −4° C., and that the impact of high RAP levels in new bituminous mixtures should be evaluated. Further, the extremely negative values of ΔTc for RAS recovered binders require additional scrutiny as to the overall impact of RAS incorporation into bituminous mixtures.

Table 2 shows that it is possible to age bituminous mixtures under laboratory aging followed by recovery of the binder from the mixtures and determination of the recovered binder ΔTc. The long term aging protocol for bituminous mixtures in AASHTO R30 specifies compacted mix aging for five days at 85° C. Some research studies have extended the aging time to ten days to investigate the impact of more severe aging. Recently, aging loose bituminous mixes at 135° C. for 12 and 24 hours and in some instances for even greater time periods have been presented as alternatives to compacted mix aging. The goal of these aging protocols is to produce rapid binder aging similar to field aging representative of more than five years in service and more desirably eight to 10 years in service. For example, it has been shown for mixtures in service for around eight years that the ΔTc of the reclaimed or recycled asphalt from the top ½ inch of pavement was more severe than 12 hours aging at 135° C. but less severe than 24 hours aging at 135° C.

The data in the first two rows of Table 2 show why long-term aging of mixtures containing recycled products is important. The binder recovered from the unaged mix (row 1) exhibited a ΔTc of −1.7° C., whereas the binder recovered from the 5 day aged mix exhibited a ΔTc of −4.6° C.

TABLE 2

| Binder recovered from RAP or RAS containing mixtures either lab or field aged | High temperature grade | Critical Low temperature stiffness grade based on 4 mm DSR | Critical Low temperature creep grade based on 4 mm DSR | ΔTc ° C. |
|---|---|---|---|---|
| Field mix 09-27-13-F PG 58-28 + 5% RAS, unaged | 83.1 | −32.3 | −30.6 | −1.7 |
| Field mix 09-27-13-E PG 58-28 + 5% RAS, 5 day aged @ 85° C. | 102.8 | −28.5 | −23.9 | −4.6 |
| US Hwy 14 PG 58-28 + 6% RAS & 11% RAP, 10 day aged @ 85° C. | 85.4 | −30.9 | −24.1 | −6.8 |
| US Hwy 14 PG 52-34 + 6% RAS & 11% RAP, 10 day aged @ 85° C. | 80.8 | −35.6 | −29.9 | −5.7 |
| US Hwy 14 PG 58-28 + 31% RAP, 10 day aged @ 85° C. | 79.5 | −29.6 | −26.7 | −2.9 |
| Core from field paved 2011, cored 2013, binder from top ½ inch of core (mix contained PG 58-28 + 5% RAS or 22% shingle binder replacement) | 87.6 | −25.9 | −21.7 | −4.2 |
| Core from field paved 2011, cored 2013, binder from second ½ inch of core below the surface (mix contained PG 58-28 + 5% RAS or 22% shingle binder replacement) | 86.0 | −25.6 | −21.9 | −3.8 |
| Core from field paved 2011, cored 2013, binder from layer 2 inches below surface (mix contained PG 58-28 + 5% RAS or 22% shingle binder replacement) | 80.7 | −26.0 | −24.2 | −1.8 |

Anti-Aging Additives

The disclosed additives can alter (e.g., reduce or retard) an asphalt binder aging rate, or can restore or renew an aged or recycled binder to provide some or all of the properties of a virgin asphalt binder. For example, the additives can alter or improve physical and rheological characteristics such as stiffness, effective temperature range, and low temperature properties of the asphalt binder.

Asphaltenes include extensive condensed ring systems with some level of unsaturation. The asphaltene content of typical binders can range from less than 10% to more than 20%. Asphaltenes are typically described as materials that are insoluble in n-heptane. An exact structure is unknown and based on the performance behavior of different binders it is unlikely that the asphaltene structure in any two binders is the same, especially those from different crude sources. Asphaltenes give a binder its color and stiffness and their levels in a binder tend to increase as the binder ages. Consequently, the addition of RAP or RAS or combinations of both causes the asphaltene content to increase. Increasing asphaltene content along with other products of oxidation such as carbonyls and sulfoxides are responsible for the stiffening of bituminous mixtures and their ultimate failure. By their very chemical nature asphaltenes are not readily soluble in aliphatic chemicals. Aromatic hydrocarbons will readily dissolve asphaltenes and aromatic process oils have been used in recycled mixtures. However these oils may contain polynuclear aromatic compounds including listed potential carcinogens and therefore are not desirable additives. Most plant based oils are straight or branched chain hydrocarbons with some level of unsaturation and therefore are not as effective at retarding aging as they are at softening the overall binders in a mixture.

Titerpenoids are a major group of plant natural products that include sterols, triterpene saponins, and related structures. Triterpenoids can be of natural or synthetic origin. Typically they are obtained by extraction from plant material. Extraction processes for the isolation of triterpenoids are described e.g., in the international applications WO 2001/72315 A1 and WO 2004/016336 A1, the disclosures of which are each incorporated herein by reference in their entirety.

The triterpenoids include and be sources for sterols and stanols. The disclosed triterpenoids refer to the non-esterified forms of any of the sterols or stanols mentioned herein. In certain embodiments, the anti-aging additive is a sterol. In certain embodiments, the anti-aging additives can be plant sterols and plant stanols. In certain embodiments, the triterpenoids can be a source of sterols.

Exemplary pure plant sterols include campesterol, stigasterol, stigmasterol, β-sitosterol, Δ5-avenosterol, Δ7-stigasterol, Δ7-avenosterol, brassicasterol or mixtures thereof. In some embodiments, the sterol blend contains β-sitosterol as the pure sterol. In other embodiments, the sterol blend contains a mixture of pure sterols. Commercially available pure sterols and mixtures of pure sterols include those available from MP Biomedicals (Catalog No. 02102886) referred to as beta-Sitosterol (beta-Sitosterol~40-60%; campesterol~20-40%; Stigmasterol~5%).

Exemplary crude plant sterols include modified or unmodified natural products containing significant quantities of sterols, including such diverse plant sources as corn oil, wheat germ oil, sarsaparilla root, soybean pitch and corn oil pitch. For example, tall oil pitch is obtained during the process of preparing paper from wood, particularly pine wood. Tall oil pitch is an extremely complex material that can contain rosins, fatty acids, oxidation products and esterified materials, an appreciable fraction of which are sterol esters. Plant sources of crude sterols are inexpensive in that they are the foots or tailings left from various manufacturing processes In some embodiments, the crude sterol sources include stigmasterol, β-sitosterol, campesterol, ergosterol, brassicasterol, cholesterol and lanosterol or mixtures thereof. In some embodiments, the crude sterol sources include soy bean oil, corn oil, rice bran oil, peanut oil, sunflower seed oil, safflower oil, cottonseed oil, rapeseed oil, coffee seed oil, wheat germ oil, tall oil, and wool grease. In some embodiments the crude sterol includes a bio-derived source or partially distilled residue of the bio-derived source. In some embodiments, the crude sterol source includes tall oil pitch, soybean oil or corn oil.

Any of the oil tailings or pitches from the disclosed plant sources is suitable crude sterol sources. U.S. Pat. No. 2,715,638, Aug. 16, 1955, to Albrecht, discloses a process for recovering sterols from tall oil pitch whereby the fatty acid impurities are removed by a neutralization process. Following this, the sterol esters are saponified; the free sterols are then recovered and washed with isopropanol and dried. If sufficiently purified, the recovered free sterols may be used as pure sterols rather than as crude sterols.

The crude sterols preferably are obtained from plant sources. The crude sterol can include components in addition to the desired sterol or sterols. Exemplary plant sources for crude sterols include tall oil pitch, crude tall oil, sugar cane oil, hot well skimmings, cottonseed pitch, soybean pitch, corn oil pitch, wheat germ oil or rye germ oil. In some embodiments, tall oil pitch is a source of the crude sterol. Tall oil pitch can include about 30 to 40% unsaponifiable molecules. Unsaponifiables are molecules that do not react with alkali hydroxides. Fatty and rosin acids remaining in the tall oil pitch readily react with potassium or sodium hydroxides and thus the unsaponifiables can be readily separated. It has been shown that 45% of the unsaponifiable fraction can include sitosterols. Therefore, a tall oil pitch sample can contain approximately 13.5% to 18% sterol molecules by weight.

In some embodiments, the additive can be an animal sterol such as cholesterol.

One of skill in the art will understand that a triterpenoid can be used as a source of sterols The source of sterols can be used as an anti-aging additive in an amount effective to provide a less negative $\Delta Tc$ value after aging the asphalt binder compared to a similarly-aged binder without the anti-aging additive. In certain embodiments, the anti-aging additive can provide an asphalt binder a $\Delta Tc$ of greater than or equal to −5.0° C. As shown herein, pure sterol (e.g. 5%) retards aging better than other additives as shown by the $\Delta Tc$ value.

The additive added to the asphalt may for example range from about 0.5 wt. %, to about 15 wt. %, or about 1 wt. %, to about 10 wt. %, about 1 wt. % to about 3 wt. %, about 3 wt. %, to about 5 wt. %, about 5 wt. % to about 10 wt. %, about 10 wt. % to about 15 wt. %, of the virgin binder in an asphalt.

In some embodiments, the sterol can provide an asphalt binder with a $\Delta Tc$ of greater than or equal to −5.0° C. In some embodiments, the sterol can provide an asphalt binder with a $\Delta Tc$ of greater than or equal to −5.0° C. after 40 hours of PAV aging. In still other embodiments, the sterol can provide an asphalt binder with a less negative $\Delta Tc$ value and a decreased R-Value following aging, when compared to a similarly-aged asphalt binder without the sterol.

It should be noted that the terms "mixed sterol" or "sterol blends" or "sterol in blend" or grammatically equivalent phrases have been used interchangeably to refer to pure sterols.

Softening Agents & Other Additives

Softening agents that may be used in binders include waste engine oil and waste engine oil that may be further processed to provide REOB. REOB is a low cost softening additive and asphalt extender obtained from the residual material remaining after the distillation of waste engine oil either under vacuum or at atmospheric pressure conditions. The distilled fraction from the re-refining process is converted into new lubricating oil for vehicles, but the bottoms do not have an available market due to the presence of metals and other particulates from internal combustion engines. Also these bottoms contain paraffinic hydrocarbons and additives incorporated into the original lubricating oil. For many years REOB were used by some companies as an asphalt extender, but the usage was localized.

Greater amounts of waste engine oils are being re-refined and therefore greater amounts of REOB are being sold into the asphalt binder market. The use of REOB may result in bituminous mixtures, which when aged, exhibit $\Delta Tc$ values of −4° C. or lower with consequent poor performance in pavements. When REOB are added to some asphalts at levels as low as 5% by weight, the resulting $\Delta Tc$ after 40 hr. PAV aging can be −5° C. or lower (viz., more negative). Recovered binders from field mixes shown to contain REOB by means of metals testing have shown greater distress than field mixtures of the same age and the same aggregate and paved at the same time but not containing REOB.

The disclosed sterol can mitigate the impact of waste engine oils (e.g. REOB) on $\Delta Tc$ (as evaluated, for example, using 40 hr. of PAV aging) and renew or retard the aging rate of the recycled asphalt.

The disclosed sterol can also be used to mitigate the impact of other softening agents, which behave similarly to REOB. In other words, the other softening agents are agents when aged, have $\Delta Tc$ values of −4° C. or lower with consequent poor performance in pavements. These other softening agents include synthetic or virgin lubricating oils (such as MOBIL™ 1 synthetic oil from ExxonMobil Corp. and HAVOLINE™ 10W40 oil from Chevron USA Inc.), virgin paraffin or naphthenic base oils, untreated or non-rerefined waste drain oils or waste engine oil materials, vacuum tower asphalt extenders (the non-distillable fraction from re-refining used engine oil) and paraffinic or naphthenic process oils.

It should be noted that softening agents such as bioderived softening agents (e.g. Cargill's 1103 and Arizona Chemical's RS1100) can soften an asphalt binder without adversely affecting the asphalt binder in the same manner as REOB. The sterol can retain much of the beneficial softening of these bioderived softening agents.

The asphalt may contain other components in addition to the disclosed sterol. Such other components can include elastomers, non-bituminous binders, adhesion promoters, softening agents, rejuvenating agents and other suitable components.

Useful elastomers include, for example, ethylene-vinyl acetate copolymers, polybutadienes, ethylene-propylene copolymers, ethylene-propylene-diene terpolymers, reactive ethylene terpolymers (e.g. ELVALOY™), butadiene-styrene block copolymers, styrene-butadiene-styrene (SBS) block terpolymers, isoprene-styrene block copolymers and styrene-isoprene-styrene (SIS) block terpolymers, chloroprene polymers (e.g., neoprenes) and the like. Cured elastomer additives may include ground tire rubber materials.

In one embodiment, the binder includes a blend of binders. In certain embodiments, the binder blend includes virgin binder and binder extracted from reclaimed asphalt. For example, the binder extracted from RAS material may be extracted from manufacturer asphalt shingle waste, from consumer asphalt shingle waste, or from a mixture of binders extracted from manufacturer and consumer asphalt shingle waste. In certain embodiments, a binder blend may include from about 60 wt % to about 95 wt % of virgin binder and from about 5 wt % to about 40 wt % of binder extracted from reclaimed asphalt such as RAS. In certain embodiments, the binder blend includes the addition of an anti-aging additive from about 0.5 wt % to about 15.0 wt % of the virgin asphalt. In certain embodiments, the binder blend can include the addition of from about 0.2 wt % to about 1.0 wt % anti-aging additive. The anti-aging additive has been shown to improve high and low temperature properties and PG grading for both low and high temperature ends of RAS-containing asphalt binder blends.

The asphalt binder may be prepared by mixing or blending the sterol with the virgin binder to form a mixture or blend. The mixture or blend can be added to recycled asphalt materials (e.g. RAS and/or RAP) and aggregate. One of skill in the art will recognize that any sequences of adding and mixing components are possible. Asphalt can be prepared by applying mechanical or thermal convection. In one aspect, a method of preparing an asphalt involves mixing or blending a sterol with virgin asphalt at a temperature from about 100° C. to about 250° C. In some embodiments, the sterol is mixed with the virgin asphalt at a temperature from about 125° C. to about 175° C., or 180° C. to about 205° C. In some embodiments, the asphalt is mixed with asphalt, sterol and softening agent. In still other embodiments, the asphalt is mixed with asphalt, RAS, RAP, or combinations of RAS and RAP, sterol and aggregate.

The disclosed asphalt can be characterized according to ASTM specifications and test methods, in addition to many standard tests. For example, the disclosed asphalts and binders can be characterized using rheological tests (viz., dynamic shear rheometer, rotational viscosity, and bending beam).

At low temperatures (e.g., −10° C.), road surfaces need cracking resistance. Under ambient conditions, stiffness and fatigue properties are important. At elevated temperature, roads need to resist rutting when the asphalt becomes too soft. Criteria have been established by the asphalt industry to identify rheological properties of a binder that correlate with likely paved road surface performance over the three common sets of temperature conditions.

To determine the ΔTc parameter, a 4 mm DSR test procedure as described above and developed by Western Research Institute (Sui, C., Farrar, M., Tuminello, W., Turner, T., A New Technique for Measuring low-temperature Properties of Asphalt Binders with Small Amounts of Material, Transportation Research Record: No 1681, TRB 2010. See also Sui, C., Farrar, M. J., Harnsberger, P. M., Tuminello, W. H., Turner, T. F., New Low Temperature Performance Grading Method Using 4 mm Parallel Plates on a Dynamic Shear Rheometer. TRB Preprint CD, 2011) can be used.

The ΔTc parameter can also be determined using the Bending Beam Rheometer (BBR) test procedure based on AASHTO T313 or ASTM D6648. It is important that when the BBR test procedure is used that the test is conducted at a sufficient number of temperatures such that results for the Stiffness failure criteria of 300 MPa and Creep or m-value failure criteria of 0.300 are obtained with one result being below the failure criteria and one result being above the failure criteria. In some instances for binders with ΔTc values less than −5° C. this can require performing the BBR test at three or more test temperatures. ΔTc values calculated from data when the BBR criteria requirements referred to above are not met are not considered to be completely accurate.

The surface characteristics and changes can be revealed in an asphalt. These surface characteristics can be determined using atomic force microscopy (AFM). AFM is described in the following references R. M. Overney, E. Meyer, J. Frommer, D. Brodbeck, R. Lüthi, L. Howald, H. J. Güntherodt, M. Fujihira, H. Takano, and Y. Gotoh, "Friction Measurements on Phase-Separated Thin Films with a Modified Atomic Force Microscope", Nature, 1992, 359, 133-135; E. zer Muhlen and H. Niehus, "Introduction to Atomic Force Microscopy and its Application to the Study of Lipid Nanoparticles", Chapter 7 in Particle and Surface Characterization Methods, R. H. Muller and W. Mehnert Eds, Medpharm Scientific Pub, Stuttgart, 1997; H. Takano, J. R. Kenseth, S. S. Wong, J. C. O'Brien, M. D. Porter, "Chemical and Biochemical Analysis Using Scanning Force Microscopy", Chemical Reviews 1999, 99, 2845-2890.

AFM is a type of scanning microscopy that provides high resolution, three-dimensional imaging at the atomic and molecular level. AFM can be used for both topographical imaging and force measurements. Topographical imaging involves scanning the cantilever/tip across the sample surface. A laser beam is reflected off the back of the cantilever, and small changes in cantilever deflection are detected with a position-sensitive photodiode detector. This deflection is processed by the system electronics to determine topological height changes on the sample surface.

Surface defects may be measured as the surface roughness, expressed as average roughness over an image surface, the average height of the roughness extending out of the surface of the sample, the defect area (i.e. the non-smooth plane of the sample) expressed in μm2 and the defect area expressed as a percent keeping in mind that the area of each image is 400 µm2. AFM can be used to determine the effects of the disclosed anti-aging additives on an asphalt. AFM was used to determine the effects of sterol as disclosed in PCT International Application No. PCT/US16/37077 filed Jun. 10, 2016 and in U.S. Provisional Application No. 62/385,899, filed Sep. 9, 2016, each of which is incorporated herein by reference in its entirety.

Figure 13:
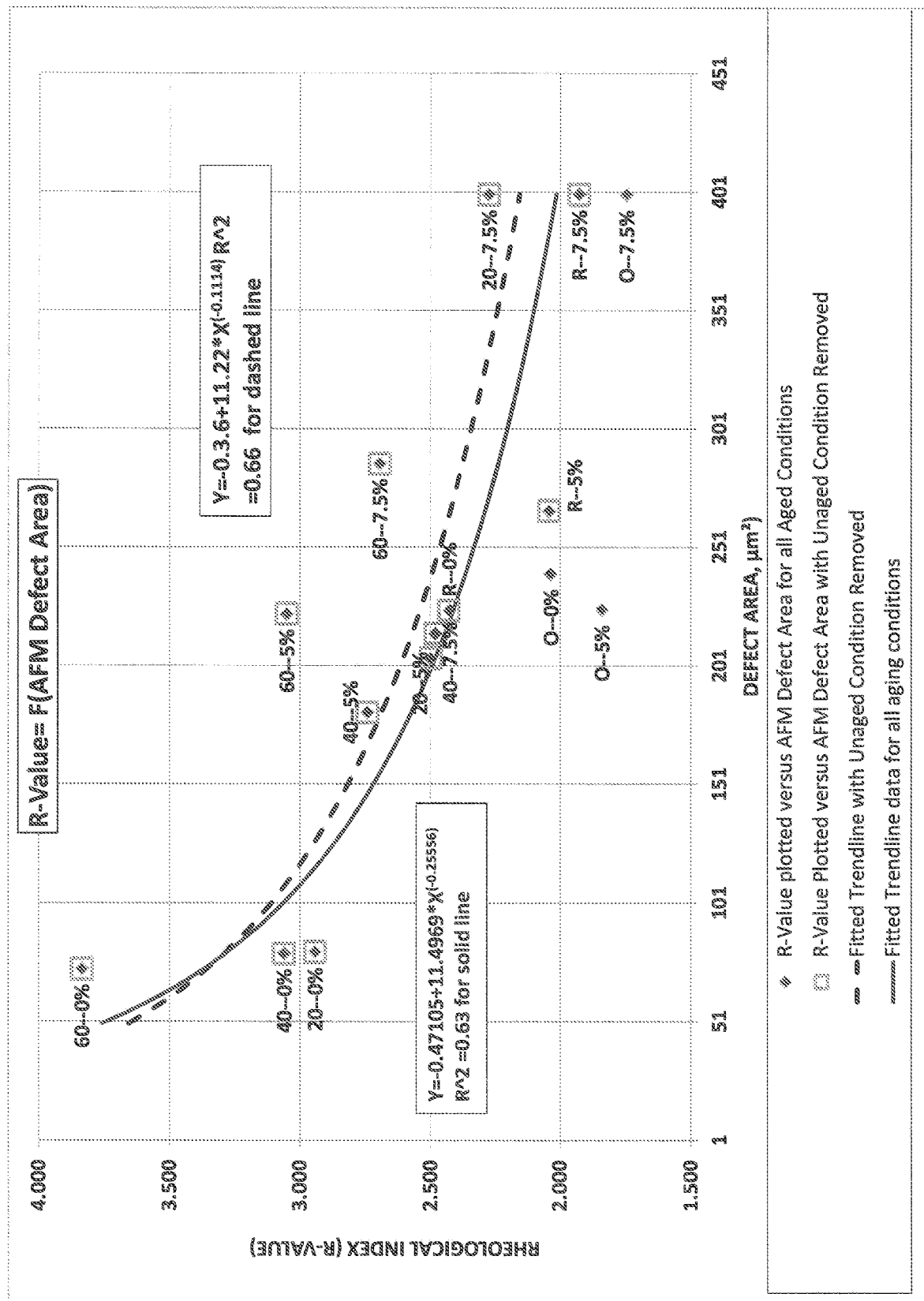
FIG. 13 is a graphical representation of R-Value versus AFM surface defect area for all samples and for samples with the unaged binder data removed.

Applicants have discovered that as binders age, with different sterol levels there can be variation in the amount of "surface defects" that developed in the material being imaged. It is well known to one skilled in the art that as binders age chemical changes occur due to oxidation and heat. These are manifested, and shown herein, as decreases in Colloidal Index, increases in R-Value and more negative values of $\Delta Tc$. Through AFM images it was observed that as aging occurred and as the sterol level increased, the surface roughness of the area being imaged increased. However for any given sterol level as binder aging increased the areas of the surface that protruded from and accumulated on the surface of the imaged region decreased. Without being bound by any particular theory, the sterol may function to agglomerate or accumulate materials in the binder that may otherwise cause an increase in R-Value, decrease in $\Delta Tc$ (more negative values), and decrease in Colloidal Index, and thereby isolate such materials within the overall asphalt bulk material. Such a mechanism would in effect sequester those materials responsible for binder degradation and thereby retard the rate at which deleterious changes in properties might otherwise be observed. The data shows that as aging increases, the ability of a given level of sterol to continue to sequester these deleterious components diminishes as presumably more of such deleterious components are produced as the binder ages. FIG. 13 shows that the binder samples with the lowest level of defects are the 20, 40 and 60 hour PAV residues with no sterol addition. In effect the species produced by aging are spread throughout the binder and alter the rheological and chemical identifiers of aging to a negative extent.

Applicants have also discovered a relationship between the chemical compositional changes captured by an Iatroscan procedure and the changes occurring at the molecular level captured by AFM when significant aging was studied. As the area occupied by the surface defects decreases the Colloidal Index decreases which represents a more aged material.

Asphalt is a colloidal system in which the most important structure forming elements are the asphaltenes, which are dispersed in the maltenes. The size of the colloidal particles can be determined using different techniques: ultrafiltration, electron microscopy, small angle X-ray scattering and others. Two parameters that control the stability of asphaltene micelles are the ratio of aromatics to saturates and that of resins to asphaltenes. When these ratios decrease, asphaltene micelles will coalesce and form larger aggregates.

Asphalt samples can be fractionated into asphaltenes and maltenes using n-heptane (ASTM D3279). The asphaltenes can be precipitated while the soluble maltenes can be obtained as filtrates and subsequently fractionated by liquid chromatography into resins, aromatics and saturated fractions. The resins can be first adsorbed and eluted from solid adsorbents followed by the recovery of the oils. The oils can be fractionated into other components: saturates, monocyclic aromatics, bicyclic aromatics and polycyclic aromatics asphaltenes, resins, aromatics and saturates, mostly called SARA, and can be determined by various methods, for example, by relying on solubility of the particular chemical groups of bitumen based on polarity. One such method that can be used to quantify three generic fractions of the maltene fraction of an asphalt can be the thin-layer chromatography-flame ionization detection (TLC-FID), also known as an Iatroscan procedure. The three generic fractions determined in the Iatroscan procedure are resins, aromatics and saturates; the asphaltenes having been determined using ASTM D3279.

As the binder ages the asphaltenes increase and generally the cyclics decrease; the saturate content does not change appreciably and the resins increase but not to the same extent at which the cyclics decrease. The overall result is that as the binder ages the Colloidal Index decreases as a result of changes to amounts of these four fractions in the binder. The reciprocal of the CI value is known as the Colloidal Instability Index (CII) and may also be used to characterize aging.

The colloidal index (CI) can be calculated from the percentage values for four fractions determined from an Iatroscan procedure. The calculation for CI is:

$$CI=(Cyclics+Resins)/(Asphaltenes+Saturates)$$

As the binders age the general trend is for the defect area or surface roughness to decrease. This may be interpreted to mean that initially the components that result in binder degradation are agglomerated and as they age these components oxidize resulting in chemical changes that cause the Colloidal Index to decrease. Primarily these changes appear to be an increase in asphaltenes and decrease in cyclics. These chemical changes appear to reduce the ability of the binder to relax stresses as manifested by increases in R-Value and decreases in $\Delta Tc$. The presence of the sterol additive appears to remove those components that cause property degradation (also referred to as deleterious components) and render them less effective than they would otherwise be. As the data shows, this retardation of degradation is not a permanent change in the binder but can substantially extend the time before the binder will reach a state of degradation were the sterol not present.

In one embodiment a method for identifying aging in an asphalt, wherein the aging is identified by surface defects or average roughness using AFM, and wherein the asphalt is determined as aged if the surface defects or average roughness decrease. In other embodiments, AFM is used in a method for identifying an aged asphalt that includes analyzing the asphalt for the presence or absence of surface roughness or surface defects by AFM, wherein the sample is identified as aged if reduced surface roughness is detected.

In some embodiments, a method for identifying aging in an asphalt or binder and slowing aging or restoring of the aged asphalt or aged binder includes analyzing asphalt or binder for the presence or absence of surface defects, wherein the asphalt or binder is determined as aging or aged if minimal surface defects are detected; and adding a sterol additive and virgin binder to the aged asphalt or binder to reduce or slow further aging. In some embodiments, the aged asphalt include recycled asphalts, softening agents, and rejuvenating agents. For example, some asphalt include RAS, RAP, REOB, virgin paraffinic base oils, untreated or non-rerefined waste drain oils or waste engine oil materials, vacuum tower asphalt extenders, paraffinic or naphthenic processing oils and lubricating base oils. In certain embodiments, an effective amount of an anti-aging additive can provide a less negative $\Delta Tc$ value after aging the asphalt binder compared to a similarly-aged binder without the anti-aging additive. In some embodiments, the anti-aging additive can provide a less negative $\Delta Tc$ value after aging an asphalt binder compared to a similarly-aged binder without the anti-aging additive. The asphalt binder can include for example at least 3% or greater RAS, at least 25% or greater RAP, at least 5% REOB or greater, at least 5% or greater paraffinic oils.

In some embodiments, the average roughness of an asphalt or binder with sterol additive is 1.5 to 350 µm², 3.6 to 232 µm², or 10 to 230 µm².

The invention is further illustrated in the following non-limiting examples, in which all parts and percentages are by weight unless otherwise indicated.

Example 1

To investigate the efficacy of the anti-aging additive, four binders were produced and aged for 20 and 40 hours in the PAV (Pressured aging vessel) following ASTM D65217.

The binders were produced by mixing the components with a low shear Lightning mixer in a 1 gallon can at a temperature of 187.8° C.-204° C. (370-400° F.) for approximately 30 minutes. The test results for all binders used are shown in Table 3.

Sample #1 consisted of 80% PG 52-34 blended with 20% binder recovered from manufacturer's waste shingles obtained from Recovery Technology Solutions (RTS), Shakopee, Minn. and no sterol.

Sample #2 consisted of 90% PG 58-28 blended with 10% binder recovered from post-consumer waste shingles obtained from Recovery Technology Solutions (RTS), Shakopee, Minn. and contained no sterol.

Sample #3 consisted of 75% of a conventional PG 52-34 binder, 20% binder recovered from manufacturer's waste shingles obtained from Recovery Technology Solutions (RTS), Shakopee, Minn. and 5% mixed sterols obtained from MP Biomedicals (Catalog No. 02102886) referred to as beta-Sitosterol (beta-Sitosterol ~40-60%; campesterol~20-40%; Stigmasterol-5%).

Sample #4 consisted of 72.5% of a conventional PG 58-28 binder, 20% binder recovered from post-consumer waste shingles obtained from Recovery Technology Solutions (RTS), Shakopee, Minn. and 7.5% of mixed sterols obtained from MP Biomedicals (Catalog No. 02102886) referred to as beta-Sitosterol (beta-Sitosterol ~40-60%; campesterol~20-40%; Stigmasterol-5%).

The high temperature binder grade for binders in the unaged condition is the temperature at which the binder stiffness equals 1 kiloPascal (kPa) when tested in accordance with ASTM D7175. The high temperature stiffness grade for binders in all other aged conditions is the temperature at which the binder stiffness equals 2.2 kPa when tested in accordance with ASTM D7175. This convention is in keeping with typical SHRP PG grading practices. The results in Table 3 show that when no sterol is present in the sample the high temperature grade increases at a faster rate than when sterol is present. For Sample #1 the high temperature stiffness grade after the 20 hour PAV was 5.1° C. higher than Sample #3. After the 40 hour PAV the difference was 6.5° C., or one full PG grade greater in high the high temperature grade. For Sample #2 (with only 10% recovered shingle binder) with no sterol has a high temperature grade that is 3.2° C. higher than Sample #4 with 20% recovered shingle binder and 7.5% sterol after the 20 hour PAV and a stiffness grade 5.8° C. higher after the 40 hour PAV. The impact on low temperature properties is similar in scope. After 20 hours of PAV aging Sample #4 still has a positive ΔTc of 1.3° C. which is beneficial difference of 2.9° C. After 40 hours PAV aging the ΔTc of Sample #4 is −1.9° C. which is 2.8° C. better than Sample #2. These are significant improvements considering that Sample #2 contained half the amount of recovered shingle binder as compared to Sample #4. The data summarized in Table 3 shows that not only does the use of sterol retard the impact of aging on low temperature properties, especially the critical relaxation property related to the m-value, but sterol addition also slows the rate at which the high temperature stiffness of the binder increases with age.

TABLE 3

| Binder | % RTS shingle binder | % Sterol | Aging | High Temp Grade | S-Critical Temp | m-Critical Temp | ΔTc |
|---|---|---|---|---|---|---|---|
| PG 52-34 | 20 | 0 | Unaged | 59.8 | −36.2 | −39.8 | 3.6 |
| PG 52-34 | 20 | 0 | RTFO | 60.7 | −37.0 | −38.2 | 1.2 |
| PG 52-34 | 20 | 0 | 20 hr. | 74.8 | −34.7 | −33.1 | −1.6 |
| PG 52-34 | 20 | 0 | 40 hr. | 83.2 | −34.3 | −29.6 | −4.7 |
| PG 58-28 | 10 | 0 | Unaged | 63.9 | −34.3 | −36.7 | 2.4 |
| PG 58-28 | 10 | 0 | RTFO | 66.5 | −32.2 | −33.1 | 0.9 |
| PG 58-28 | 10 | 0 | 20 hr. | 77.9 | −31.7 | −30.5 | −1.2 |
| PG 58-28 | 10 | 0 | 40 hr. | 87.2 | −30.0 | −26.0 | −4.0 |
| PG 52-34 | 20 | 5 | Unaged | 57.8 | −37.4 | −40.8 | 3.4 |
| PG 52-34 | 20 | 5 | RTFO | 57.8 | −36.6 | −39.5 | 2.9 |
| PG 52-34 | 20 | 5 | 20 hr. | 69.7 | −32.8 | −34.0 | 1.2 |
| PG 52-34 | 20 | 5 | 40 hr. | 76.7 | −33.5 | −31.6 | −1.9 |
| PG 58-28 | 20 | 7.5 | Unaged | 63.2 | −33.5 | −36.1 | 2.6 |
| PG 58-28 | 20 | 7.5 | RTFO | 64.0 | −32.7 | −35.6 | 2.9 |
| PG 58-28 | 20 | 7.5 | 20 hr. | 74.7 | −29.7 | −31.0 | 1.3 |
| PG 58-28 | 20 | 7.5 | 40 hr. | 81.4 | −27.5 | −26.4 | −1.0 |

Example 2

To evaluate whether the use of mixed sterols could mitigate the excessive ΔTc results observed with REOB, three binder samples were evaluated. The samples were produced by mixing in a 1 quart can with a low shear Lightning mixer at a temperature of 300-325° F. for about 30 min. The REOB samples require less heat compared to the samples with recovered shingle binder as in Example 1.

Figure 2:
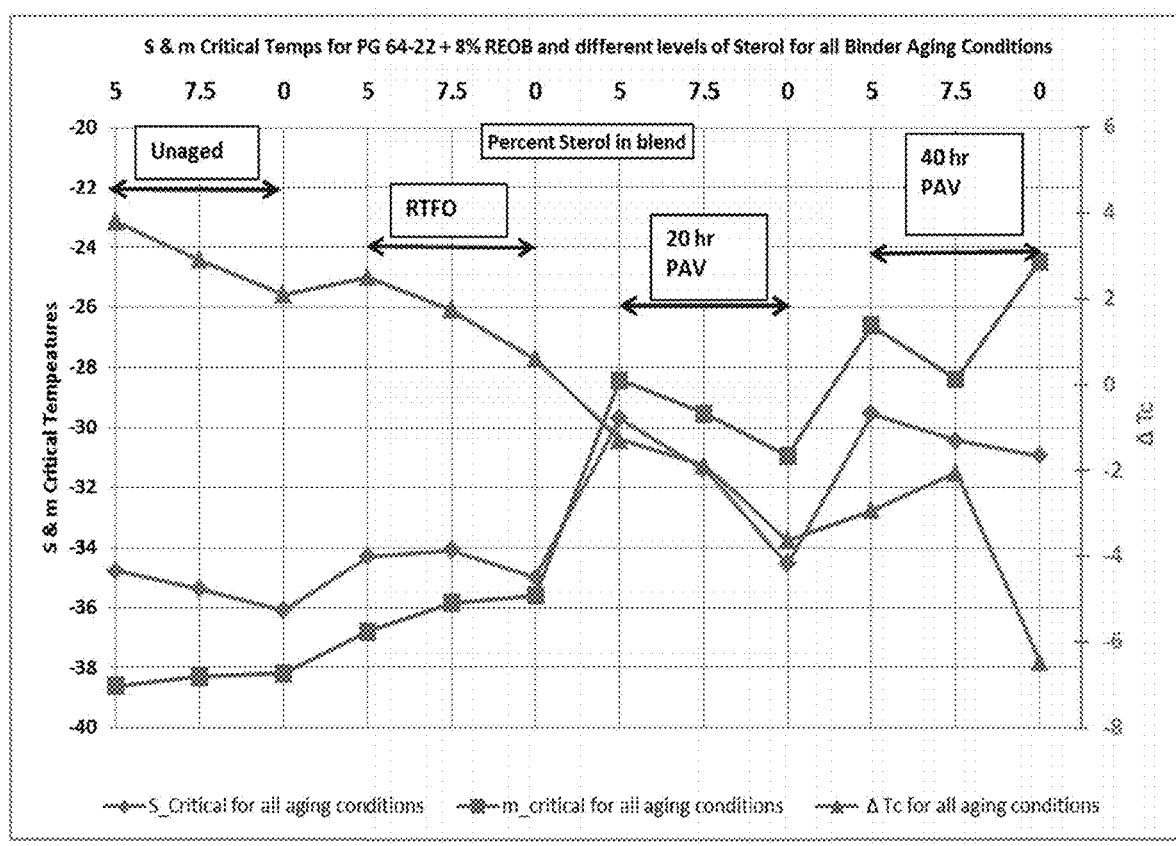
FIG. 2 is a graphical representation showing stiffness and creep temperature results for REOB samples with sterols.
Figure 3:
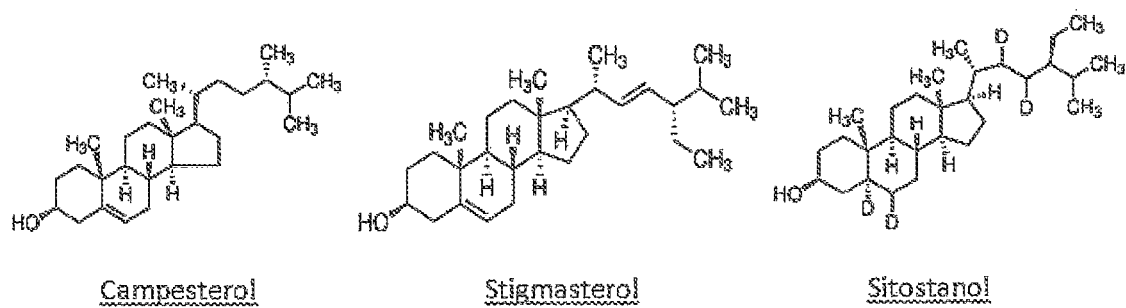
FIG. 3 shows exemplary plant sterols.

The results are shown in Table 4 and plotted in FIG. 2.

TABLE 4

| Sample description | Binder Aging | % Sterol | % REOB | S_critical | m_critical | ΔTc |
|---|---|---|---|---|---|---|
| RHEA G(t) @ −24° C. 1531, 06-03-15-G, MIA 64-22 (Tk 6 Winter Fill), 8% REOB, , 4 mm, HR3-2, HR3-2 | unaged | 0 | 8 | −36.1 | −38.2 | 2.1 |
| G(t) @ −30° C. 1531, RHEA G(t) @ −24° C. 1531, 05-28-15-B, MIA 64-22 (Tk 6), | unaged | 5 | 8 | −34.8 | −38.6 | 3.8 |

TABLE 4-continued

| Sample description | Binder Aging | % Sterol | % REOB | S_critical | m_critical | ΔTc |
|---|---|---|---|---|---|---|
| 8% REOB, 5% Plant Sterols, , 4 mm, HR3-4 | | | | | | |
| RHEA G(t) @ −24° C. 1531, 05-28-15-C, MIA 64-22 (Tk 6), 8% REOB, 7.5% Plant Sterols, 4 mm, HR3-2 | unaged | 7.5 | 8 | −35.4 | −38.3 | 2.9 |
| RHEA G(t) @ −24° C. 1531, 06-03-15-G, MIA 64-22 (Tk 6 Winter Fill), 8% REOB, , 4 mm, HR3-2, HR3-2 | RTFO | 0 | 8 | −35.0 | −35.6 | 0.6 |
| G(t) @ −30° C. 1531, RHEA G(t) @ −24° C. 1531, 05-28-15-B, MIA 64-22 (Tk 6), 8% REOB, 5% Plant Sterols, , 4 mm, HR3-4 | RTFO | 5 | 8 | −34.3 | −36.8 | 2.5 |
| RHEA G(t) @ −24° C. 1531, 05-28-15-C, MIA 64-22 (Tk 6), 8% REOB, 7.5% Plant Sterols, 4 mm, HR3-2 | RTFO | 7.5 | 8 | −34.1 | −35.8 | 1.8 |
| RHEA G(t) @ −24° C. 1531, 06-03-15-G, MIA 64-22 (Tk 6 Winter Fill), 8% REOB, , 4 mm, HR3-2, HR3-2 | 20 hr. PAV | 0 | 8 | −34.6 | −30.9 | −3.6 |
| G(t) @ −30° C. 1531, RHEA G(t) @ −24° C. 1531, 05-28-15-B, MIA 64-22 (Tk 6), 8% REOB, 5% Plant Sterols, , 4 mm, HR3-4 | 20 hr. PAV | 5 | 8 | −29.7 | −28.4 | −1.3 |
| RHEA G(t) @ −24° C. 1531, 05-28-15-C, MIA 64-22 (Tk 6), 8% REOB, 7.5% Plant Sterols, Unaged, 4 mm, HR3-2 | 20 hr. PAV | 7.5 | 8 | −31.4 | −29.5 | −1.9 |
| RHEA G(t) @ −24° C. 1531, 06-03-15-G, MIA 64-22 (Tk 6 Winter Fill), 8% REOB, , 4 mm, HR3-2, HR3-2 | 40 hr. PAV | 0 | 8 | −30.9 | −24.5 | −6.5 |
| G(t) @ −30° C. 1531, RHEA G(t) @ −24° C. 1531, 05-28-15-B, MIA 64-22 (Tk 6), 8% REOB, 5% Plant Sterols, , 4 mm, HR3-4 | 40 hr. PAV | 5 | 8 | −29.6 | −26.6 | −2.9 |
| RHEA G(t) @ −24° C. 1531, 05-28-15-C, MIA 64-22 (Tk 6), 8% REOB, 7.5% Plant Sterols, , 4 mm, HR3-2 | 40 hr. PAV | 7.5 | 8 | −30.4 | −28.4 | −2.0 |

As the binder aged, the ΔTc value for the samples with zero percent sterol exhibited the lowest value ΔTc. At 40 hr. PAV aging the ΔTc result for both the 5% and 7.5% sterol blends were greater than −3.0° C. while the zero percent sterol blend had a ΔTc value of −6.5° C.

Example 3

To evaluate whether the use of mixed sterols could mitigate the excessive ΔTc results observed with REOB in binders, three samples were evaluated. The samples were produced by mixing in a 1 quart can with a low shear Lightning mixer at a temperature of 300-325° F. for about 30 min. The REOB samples require less heat compared to the samples with recovered shingle binder as in Example 1. The mixed sterols used are the same as those described in Example 1.

The binder used in this is example was one of four binders used on a research project on County Trunk Highway 112 in Olmsted County, Minn. that was constructed in 2006. Three other binders from other crude sources were also evaluated using identical aggregate blends. The test section containing the MN1-4 binder performed significantly more poorly than the other test sections and MN1-4 contained REOB. The REOB content was not specifically provided, but testing for the zinc content of the binder indicated that the REOB content would have been in the range of 8% to 9%.

Using the MN1-4 binder samples s were produced using 5% and 7.5% sterol and aged for 20, 40 and 60 hours of PAV conditioning. Low temperature properties and ΔTc values were measured using the 4 mm DSR test procedure for an unaged, RTFO, 20, 40 and 60 hour PAV aging conditions.

Table 5 shows the comparison of total distress data obtained by an independent survey versus 40 hour PAV ΔTc data for the CTH 112-test sections. Test results for the of 5% and 7.5% sterol blends with MN1-4 binder and aged for 40 and 60 hours in the PAV are also shown.

Figure 4:
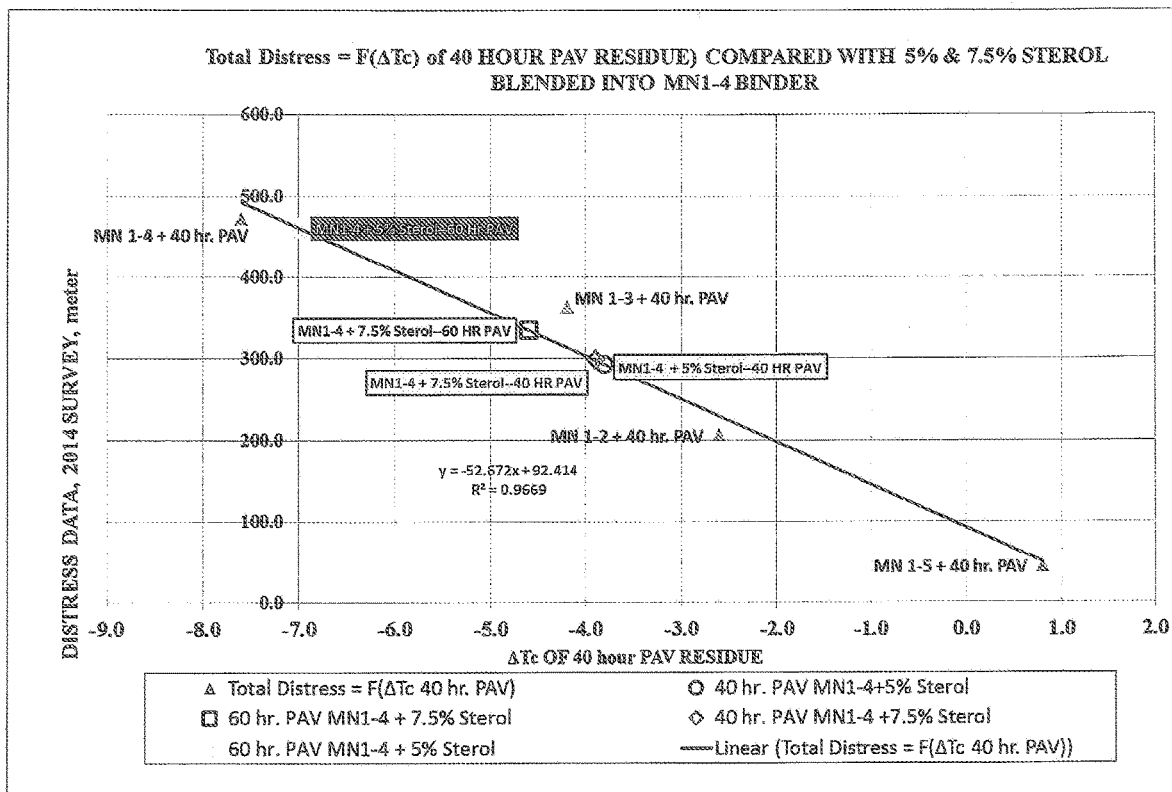
FIG. 4 is a graphical representation showing a change in $\Delta Tc$ with level of sterol and binder aging.

The data in Table 5 are also plotted in FIG. 4.

TABLE 5

| | | | ΔTc for Sterol blends in MN1-4 aged for 40 and 60 hour PAV | | | |
|---|---|---|---|---|---|---|
| Binder | TOTAL DISTRESS | ΔTc 40 Hr. PAV | MN1-4 + 5% Sterol 40 hr. PAV | MN1-4 + 7.5% Sterol 40 hr. PAV | MN1-4 + 7.5% Sterol 60 hr. PAV | MN1-4 + 5% Sterol 60 hr. PAV |
| MN1-2 | 205.9 | −2.6 | | | | |
| MN1-3 | 363.4 | −4.2 | | | | |
| MN1-4 | 472.6 | −7.6 | −3.8 | −3.9 | −4.6 | −7.0 |
| MN1-5 | 44.1 | 0.8 | | | | |

Binder MN1-2 is a polymer modified PG 58-34 produced with a blend of western Canadian crudes; MN1-3 is a PG 58-28 binder from a Minnesota refinery using a blend of western Canadian crudes; MN1-4 is from a Texas refinery using a blend of Middle East crudes from Kirkuk and MN-1-1 is PG 58-34. MN1-4 contained REOB.

Only samples of MN1-4 treated with 5% and 7.5% sterol and aged for 40 and 60 hours in the PAV all exhibited ΔTc values greater than (less negative) than the 40 hour PAV of untreated MN1-4. In a direct comparison of the ΔTc values for 40 hour PAV residues the sterol treated MN1-4 had values approximately half of the untreated MN1-4 binder. The results shown in FIG. 4 suggest that had 5% sterol been used in the MN1-4 along with the REOB the pavement performance after eight years in service could have been comparable to that of the MN1-3 binder.

Example 4

To further evaluate the role of sterols on the aging characteristics of binders with reclaimed asphalt binder shingles, four samples were evaluated: a control binder and two binders blended with commercial bio-derived oils that are promoted as rejuvenating additives for use with high levels of RAP and/or RAS. The four binders were:
1. A control binder PG 52-34 with no additive
2. PG 52-34+5% mixed sterols
3. PG 58-28+5% EVOFLEX PC2106 marketed by Ingevity
4. PG 58-28+5% RS1100 marketed by Arizona Chemical To investigate the impact of reclaimed asphalt shingles on the aging characteristics of binders the binders detailed above were used to produce bituminous mixtures containing 5% RAS which were subjected to 24 hours of loose mix aging at 135° C. After this aging step the binders were extracted and recovered and tested for low temperature properties and ΔTc was calculated The samples were produced by mixing in a one quart can with a low shear Lightning mixer at a temperature of 148.9° C.-162.8° C. (300-325° F.) for about 30 min.

The samples that were produced so that the high temperature PG grade of all four binders would be approximately the same. Because the use of 5% bio-derived oil typically reduces the high temperature PG grade by 6° C. or more a PG 58-28 binder was used with the PC2106 and the RS1100.

The high temperature PG grade of each binder following ASTM D7175 or AASHTO T315 and the low temperature properties as determined from the 4 mm DSR test after 20 hours of PAV aging are shown in Table 6.

TABLE 6

| Sample | High Temp Pg Grade Unaged Binder | 20 Hr. PAV, 4 mm S Critical Grade | 20 Hr. PAV, 4 mm m Critical Grade | Low temperature grade by 4 mm DSR | ΔTc 20 HR. PAV Binder |
|---|---|---|---|---|---|
| PG 52-34 Control | 54 | −35.76 | −35.89 | −35.8 | 0.1 |
| 52-34 + 5% Sterols | 52.7 | −34.37 | −34.80 | −34.4 | 0.4 |
| PG 58-28 + 5% Evoflex PC2106 | 51.7 | −34.44 | −33.97 | −34.0 | −0.5 |
| PG 58-28, 5%, AZ Chemical RS1100 | 49.6 | −36.96 | −36.69 | −36.7 | −0.3 |

The data in Table 6 shows that although two different starting binders were used once the samples were produced with the bio-derived oils, the high temperature PG grades were nearly the same and in fact the bio-derived oil blends were slightly lower in stiffness. Conventional low temperature PG grading is determined on the binder after the 20 hour PAV aging procedure.

The low temperature PG grade data in Table 6 showed that all four binders met a PG grade of −34. Therefore prior to producing the bituminous mixtures with the 5% RAS and prior to the 24 hour aging, the mixtures had been produced with binders of very similar high and low PG grade values.

Further each unaged binder was mixed with a typical dense graded aggregate suitable for paving a road designed to carry a designed traffic life of 3 million Equivalent Single Axel Loads (ESALs) with the addition of 5% RAS. The 5% RAS contained sufficient binder to provide approximately 20% binder replacement in the mixture. Such a level of RAS in paving mixtures is currently a well-accepted practice in the bituminous paving industry. Each 3000 gram mixture was produced by blending 5% of the RAS with 95% of the 12.5 mm nominal maximum sized aggregate. The total binder content required for the mix was 5.7% but since 20% of the binder content came from the RAS, only 4.56% of each of the binder samples was added by weight of the total mix.

The mixes were produced in a bucket mixer at a target temperature of 162.8° C. (325° F.) with two minutes of mixing time and then each was placed in a pan in a layer approximately 18 inches by approximately 12 inches by approximately 2.5 inches thick. The mix was not compacted but placed in loose condition in the pan. The pans were placed in a Blue M model 166 forced draft oven at 135° C. (275° F.) and held at that temperature for 24 hours. After this period, the mixes were removed, allowed to cool to room temperature and then the binder was extracted from the mixtures using a centrifugal extractor with toluene as the solvent to remove the binder. Recovery of the extracted asphalt was accomplished using a Buchi rotary evaporator following ASTM D7906-14, Standard Practice for Recovery of Asphalt binder from Solution Using Toluene and the Rotary Evaporator. Following recovery the 4 mm DSR test was performed. The ΔTc properties of the binders recovered from the mixtures aged for 24 hours at 135° C. was determined using the 4 mm DSR. The results of those tests are shown in Table 7.

TABLE 7

| Sample | ΔTc UNAGED BINDER | ΔTc RTFO BINDER | ΔTc 20 HR. PAV BINDER | ΔTc 40 HR. PAV BINDER | ΔTc Recovered binder from 5% RAS mix aged 24 hr. @ 135° C. (275° F.) |
|---|---|---|---|---|---|
| PG 52-34 Control | 2.7 | 1.9 | 0.1 | −1.6 | −15.1 |
| 52-34 + 5% Sterols | 2.2 | 1.5 | 0.4 | 0.5 | −8.4 |
| PG 58-28 + 5% Evoflex PC2106 | 2.1 | 2.0 | −0.5 | −1.2 | −15.4 |
| PG 58-28, 5% AZ Chemical RS1100 | 3.0 | 2.2 | −0.3 | −0.3 | −14.0 |

The data in Table 7 shows that through 40 hours of PAV aging there is little difference between the low temperature S-Critical and m-critical grades and the ΔTc properties of the four binders. However Table 8 shows that once the RAS containing mixtures were produced, aged and then the binder recovered and tested it was clear that the sterol-blended binder resisted the aging and loss of binder relaxation that is characteristic of aged RAS mixtures. It should be further noted that this resistance to aging is not a function of the base binder used to produce the mixtures. The base binder used for the Evoflex PC2106 and AZ Chemical RS1100 was a PG 58-28 while the control binder and the binder used in the sterol blend was a PG 52-34. Regardless of the base binder the samples that did not contain sterol had substantially higher high temperature PG values and ΔTc values nearly twice that of the sterol blend as detailed in Table 8

Further Table 8 shows that the 24 hour, 135° C. (275° F.) conditioning had the greatest impact on the m-value Critical Temperature value when compared to the Stiffness and m-value critical data shown in Table 7. Additionally Table 8 shows that the main impact of the plant sterol additive is its ability to retard the loss of binder relaxation due to aging. Further the high temperature PG grades of the PG 52-34 control binder and the binders produced with bio derived oils are similar indicating that those additives did not function as rejuvenating materials at either high or low temperatures.

TABLE 8

| Sample | Recovered binder from 5% RAS mix aged 24 hr. @ 135° C.—High Temp PG Grade | Recovered binder from 5% RAS mix aged 24 hr. @ 135° C.—4 mm S Critical Grade | Recovered binder from 5% RAS mix aged 24 hr. @ 135° C.—4 mm m Critical Grade |
|---|---|---|---|
| PG 52-34 Control | 122.6 | −32.20 | −17.07 |
| 52-34 + 5% Sterols | 112.6 | −29.59 | −21.15 |
| PG 58-28 + 5% Evoflex PC2106 | 129.6 | −26.07 | −10.65 |
| PG 58-28, 5% RS1100 | 125.4 | −27.79 | −13.74 |

The high temperature grade of the sterol blend is 10° C. to 17° C. below the high temperature grades of the other recovered binders, which amounts to 1.5 and nearly 3 full PG grade changes between the sterol blended binder and the other binder samples. Using the 20 hour PAV aging low temperature data (Table 7) as a basis of comparison the stiffness critical values have increased by 3.6° C. (PG 52-34 control) to as much as 8.9° C. (RS1100 blend), but the m-value critical values have increased by 18.8° C. (for the PG 52-34 control, 13.6° C. (for the Sterol blend) to 23° C. for the two bio-derived oil blends. The conclusions drawn from this example are the relaxation properties are impacted more substantially by the presence of the RAS combined with the mixture aging and the sterol containing mixture was impacted the least at both the high and low temperature properties compared to the other binders.

Example 5

A sample of PG 64-22 asphalt binder obtained from Pemex Refinery in Mexico using Mayan crude was found to have very poor aging properties when subjected to up to 60 hours of PAV aging as compared to a PG 64-22 obtained from a domestic US refinery using Canadian crude. Samples were produced by adding 5% and 7.5% mixed Sterols to the Mexican asphalt binder designated as Asphalto 64-22 and similar samples were produced using the domestically produced PG 64-22. In total 6 binder samples were evaluated. The samples were produced as described in Example 1 and the sterols used are the same as were described in Example 1.

1. A control sample of Asphalto 64-22 with no additive
2. Asphalto 64-22+5% mixed sterols
3. Asphalto 64-22+7.5% mixed sterols
4. A control sample of domestic PG 64-22 with no additive
5. Domestic PG 64-22+5% mixed sterols
6. Domestic PG 64-22+7.5% mixed sterols Binders were tested in unaged, RTFO, 20 hour PAV, 40 hour PAV and 60 hour PAV aged condition. High and low temperature PG grades were determined. The low temperature results were obtained using the 4 mm DSR procedure previously described. High temperature grade was determined following ASTM D7175. Also determined was the ΔTc result at all aging conditions based on the 4 mm DSR data. Also calculated was the Rheological Index also known as R-Value from the 4 mm DSR data. Compositional data from binders in all aged conditions was measured using the Iatroscan procedure and the Colloidal Index calculated from the data. The data for all tests are summarized in Tables 11, Table 12, Table 13 and Table 14.

As a general trend, as asphalt binders age the R-value increases because of decreased ability to relax stress and the Colloidal Index decreases because the amount of asphaltenes increase while saturates remain mostly unchanged and the cyclics decrease with only modest increases in resins. Inspection of the data in Table 11 showed that as the Asphalto 64-22 binder samples with 0%, 5% and 7.5% sterol become successively more aged, the R-Value increases and the Colloidal Index decreases.

Table 10 shows a steady decrease in the value of ΔTc for each of the tested samples as aging increases, but with a much smaller decrease in ΔTc for the 5% and 7.5% sterol blends.

TABLE 10

| Base sample | Aging Condition | S_critical | m_critical | ΔTc |
|---|---|---|---|---|
| Asfalto 64-22 | unaged | −35.6 | −34.6 | −1.0 |
| Asfalto 64-22 | RTFO | −32.5 | −29.9 | −2.6 |
| Asfalto 64-22 | 20 hr. PAV | −30.0 | −23.1 | −7.0 |
| Asfalto 64-22 | 40 hr. PAV | −29.3 | −16.9 | −12.4 |
| Asfalto 64-22 | 60 hr. PAV | −28.1 | −9.9 | −18.2 |
| Asfalto 64-22, 5% sitosterol | unaged | −33.2 | −33.1 | −0.1 |
| Asfalto 64-22, 5% sitosterol | RTFO | −31.0 | −29.7 | −1.3 |
| Asfalto 64-22, 5% sitosterol | 20 hr. PAV | −28.6 | −25.6 | −3.0 |

TABLE 9

Iatroscan Test Results

| Sample | Aging Condition | 4 mm Rvalue | Asphaltenes | Resins | Cycles | Saturates | CI |
|---|---|---|---|---|---|---|---|
| Asfalto 64-22 | unaged | 2.366 | 19.6 | 23.3 | 51.0 | 6.2 | 2.880 |
| Asfalto 64-22 | RTFO | 2.915 | 22.2 | 24.0 | 47.0 | 6.7 | 2.457 |
| Asfalto 64-22 | 20 hr. PAV | 3.609 | 26.9 | 27.8 | 38.7 | 6.5 | 1.991 |
| Asfalto 64-22 | 40 hr. PAV | 4.337 | 29.6 | 31.7 | 31.7 | 6.9 | 1.737 |
| Asfalto 64-22 | 60 hr. PAV | 4.732 | 32.7 | 28.8 | 30.5 | 8.0 | 1.457 |
| Asfalto 64-22, 5% sitosterol | unaged | 1.947 | 19.0 | 28.0 | 45.9 | 7.2 | 2.821 |
| Asfalto 64-22, 5% sitosterol | RTFO | 2.561 | 22.8 | 27.5 | 42.7 | 7.0 | 2.356 |
| Asfalto 64-22, 5% sitosterol | 20 hr. PAV | 2.923 | 25.9 | 32.4 | 34.9 | 6.7 | 2.064 |
| Asfalto 64-22, 5% sitosterol | 40 hr. PAV | 3.319 | 27.4 | 35.7 | 29.4 | 6.7 | 1.909 |
| Asfalto 64-22, 5% sitosterol | 60 hr. PAV | 3.764 | 30.4 | 34.3 | 28.2 | 7.1 | 1.667 |
| Asfalto 64-22, 7.5% sitosterol | unaged | 1.970 | 18.4 | 29.9 | 44.6 | 7.1 | 2.922 |
| Asfalto 64-22, 7.5% sitosterol | RTFO | 2.257 | 21.5 | 29.7 | 41.9 | 6.8 | 2.530 |
| Asfalto 64-22, 7.5% sitosterol | 20 hr. PAV | 2.687 | 25.1 | 34.7 | 33.4 | 6.7 | 2.142 |
| Asfalto 64-22, 7.5% sitosterol | 40 hr. PAV | 3.102 | 27.6 | 36.9 | 29.0 | 6.6 | 1.927 |
| Asfalto 64-22, 7.5% sitosterol | 60 hr. PAV | 3.292 | 29.5 | 36.6 | 27.0 | 7.1 | 1.738 |

TABLE 10-continued

| Base sample | Aging Condition | S_critical | m_critical | ΔTc |
|---|---|---|---|---|
| Asfalto 64-22, 5% sitosterol | 40 hr. PAV | −26.6 | −21.9 | −4.7 |
| Asfalto 64-22, 5% sitosterol | 60 hr. PAV | −27.6 | −17.1 | −10.5 |
| Asfalto 64-22, 7.5% sitosterol | unaged | −33.5 | −33.7 | 0.2 |
| Asfalto 64-22, 7.5% sitosterol | RTFO | −30.6 | −29.9 | −0.7 |
| Asfalto 64-22, 7.5% sitosterol | 20 hr. PAV | −27.3 | −25.0 | −2.3 |
| Asfalto 64-22, 7.5% sitosterol | 40 hr. PAV | −27.0 | −23.1 | −3.9 |
| Asfalto 64-22, 7.5% sitosterol | 60 hr. PAV | −25.8 | −20.2 | −5.6 |

TABLE 11

| Base Sample | Aging Condition | 4 mm_Rvalue | Asphaltenes | Resins | Cyclics | Saturates | CI |
|---|---|---|---|---|---|---|---|
| PG 64-22, 0% Sterol | unaged | 1.464 | 14.8 | 26.9 | 53.9 | 4.4 | 4.208 |
| Tank 6, 64-22 | RTFO | 1.721 | 16.9 | 29.5 | 49.2 | 4.4 | 3.695 |
| Tank 6, 64-22 | 20 hr. PAV | 2.149 | 23.5 | 32.6 | 38.2 | 4.2 | 2.556 |
| Tank 6, 64-22 | 40 hr. PAV | 2.363 | 26.6 | 33.8 | 35.2 | 4.5 | 2.219 |
| Tank 6, 64-22 new run on 5/11/16 | 60 hr. PAV | 2.909 | 29.8 | 33.2 | 31.4 | 5.6 | 1.825 |
| PG 64-22, 5% sterol | unaged | 1.313 | 13.2 | 32.4 | 49.1 | 5.3 | 4.405 |
| Tk 6, 64-22, 5% sitosterol | RTFO | 1.486 | 16.8 | 32.9 | 44.8 | 4.8 | 3.597 |
| Tk 6, 64-22, 5% sitosterol | 20 hr. PAV | 1.899 | 22.0 | 37.4 | 35.9 | 4.7 | 2.745 |
| Tk 6, 64-22, 5% sitosterol | 40 hr. PAV | 2.196 | 25.4 | 38.6 | 31.0 | 5.0 | 2.289 |
| Tk 6, 64-22, 5% sitosterol | 60 hr. PAV | 2.422 | 27.4 | 39.3 | 28.4 | 5.1 | 2.083 |
| PG 64-22, 7.5% sterol | unaged | 1.387 | 14.4 | 34.2 | 46.4 | 5.0 | 4.155 |
| Tk 6, 64-22, 7.5% sitosterol | RTFO | 1.500 | 17.3 | 35.5 | 42.5 | 4.7 | 3.545 |
| Tk 6, 64-22, 7.5% sitosterol | 20 hr. PAV | 1.817 | 21.7 | 39.7 | 33.8 | 4.7 | 2.784 |
| Tk 6, 64-22, 7.5% sitosterol | 40 hr. PAV | 1.995 | 24.1 | 41.9 | 29.3 | 4.7 | 2.472 |
| Tk 6, 64-22, 7.5% sitosterol | 60 hr. PAV | 2.228 | 26.4 | 41.7 | 27.2 | 4.7 | 2.215 |

TABLE 12

| Base Sample | Aging Condition | S_critical | m_critical | ΔTc |
|---|---|---|---|---|
| Tank 6, 64-22 | unaged | −30.5 | −32.7 | 2.2 |
| Tank 6, 64-22 | RTFO | −27.1 | −28.1 | 1.0 |
| Tank 6, 64-22 | 20 hr. PAV | −24.9 | −24.0 | −0.9 |
| Tank 6, 64-22 | 40 hr. PAV | −23.7 | −22.2 | −1.4 |
| Tank 6, 64-22 | 60 hr. PAV | −23.2 | −18.6 | −4.6 |
| Tk 6, 64-22, 5% sitosterol | unaged | −29.5 | −31.8 | 2.3 |
| Tk 6, 64-22, 5% sitosterol | RTFO | −27.1 | −28.9 | 1.8 |
| Tk 6, 64-22, 5% sitosterol | 20 hr. PAV | −24.8 | −25.3 | 0.5 |
| Tk 6, 64-22, 5% sitosterol | 40 hr. PAV | −23.5 | −23.4 | −0.2 |
| Tk 6, 64-22, 5% sitosterol | 60 hr. PAV | −21.4 | −20.0 | −1.4 |
| Tk 6, 64-22, 7.5% sitosterol | unaged | −30.5 | −32.7 | 2.2 |
| Tk 6, 64-22, 7.5% sitosterol | RTFO | −26.9 | −28.4 | 1.5 |
| Tk 6, 64-22, 7.5% sitosterol | 20 hr. PAV | −23.9 | −25.2 | 1.4 |
| Tk 6, 64-22, 7.5% sitosterol | 40 hr. PAV | −23.0 | −22.1 | −0.8 |
| Tk 6, 64-22, 7.5% sitosterol | 60 hr. PAV | −21.9 | −20.7 | −1.2 |

Figure 5:
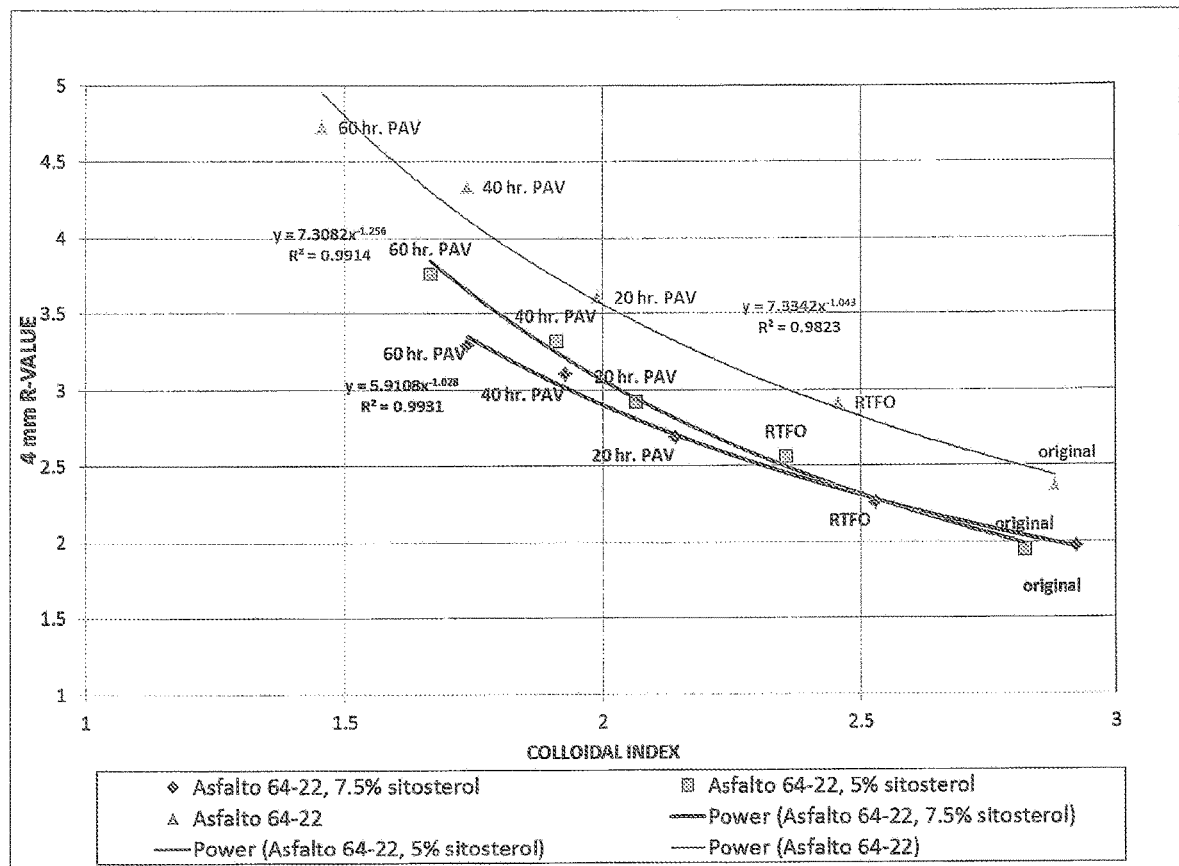
FIG. 5 is a graphical representation of R-value versus Colloidal Index for Mayan crude based Asphalto 64-22 aged through 60 hours in the PAV and for samples containing no sterol, 5% sterol, and 7.5% sterol.
Figure 6:
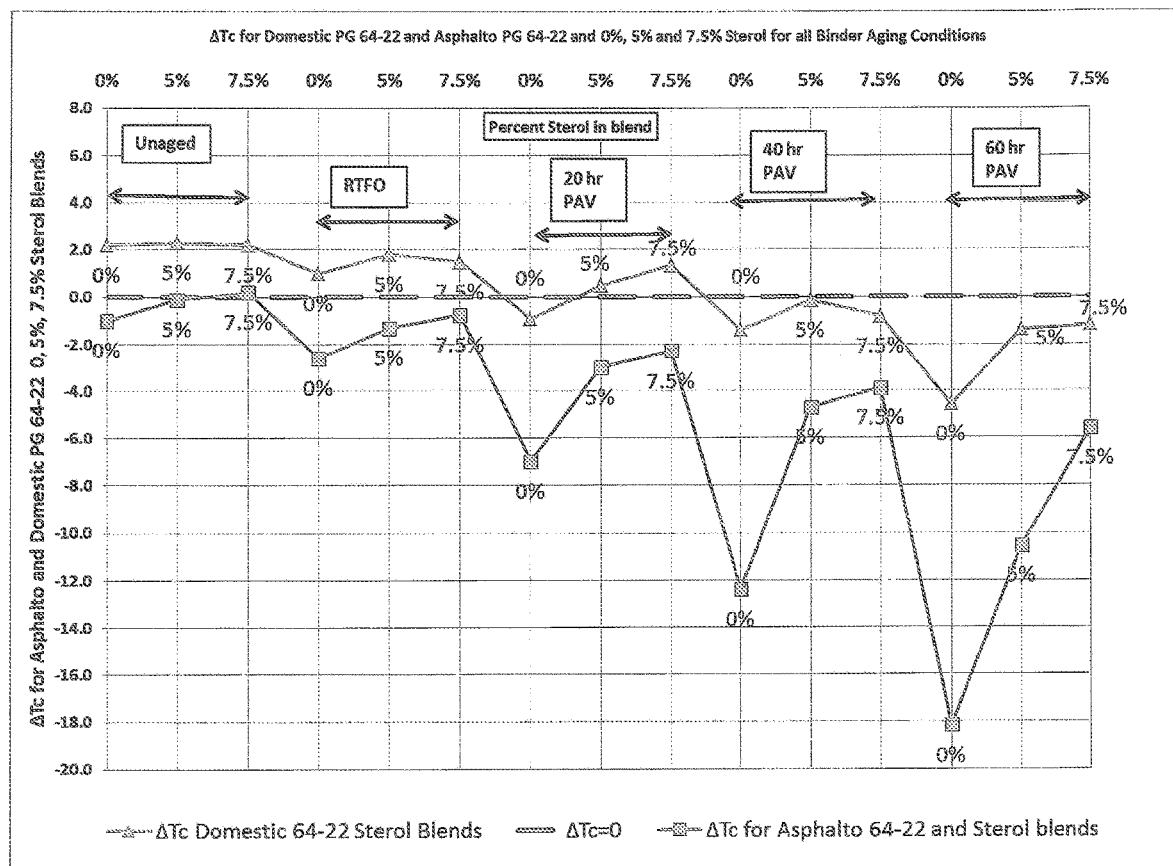
FIG. 6 is a graphical representation showing variation in $\Delta Tc$ for Mayan crude Asphalto 64-22 and Canadian crude based PG 64-22 through 60 hours of PAV aging and 0% blended sterol, 5% blended sterol and 7.5% blended sterol for both binders.
Figure 7:
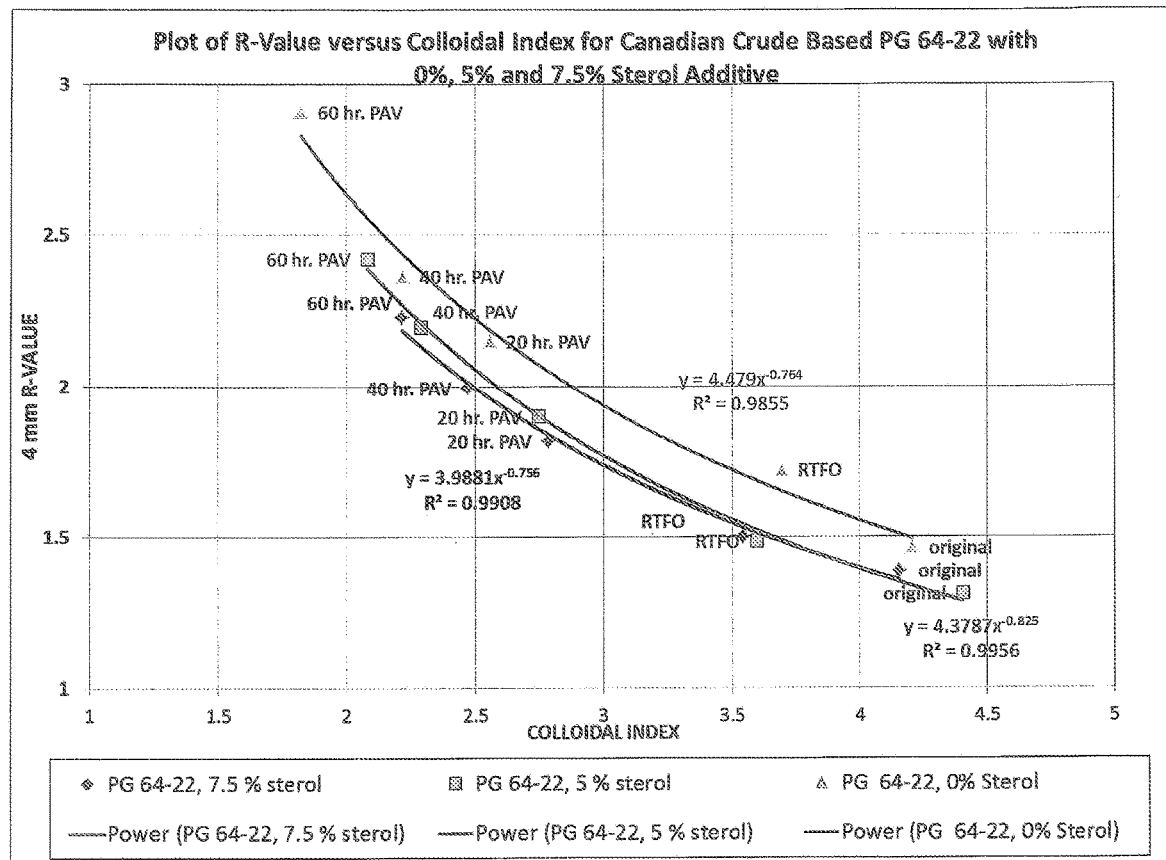
FIG. 7 is a graphical representation of R-value versus Colloidal Index for Canadian crude based PG 64-22 through 60 hours of PAV aging and containing 0% blended sterol, 5% blended sterol, and 7.5% blended sterol.

These trends are graphically depicted in FIGS. 5, 6 and 7. The data plotted in FIG. 5 shows the relationship between R-Value and Colloidal Index after various aging conditions. The R-Value-Colloidal Index curve is considerably higher for the 0% sterol blend than for the 5% and 7.5% sterol blends, whose R-Values are 0.5 or more units lower than the corresponding R-Values for the 0% sterol sample. The data also shows that after 20 hours of PANT aging there was a decrease in the R-value for the 7.5% sterol blend compared to the 5% sterol blend thus indicating that there was a dose response effect with the sterol additive for the Asphalto 64-22 binder. Since the colloidal index is a chemical constituent determination and the R-Value is a rheological determination, the high level of correlation between these two parameters suggests that the impact of the sterol has a chemical compositional as well as a rheological basis.

FIG. 6 is a plot of the ΔTc data obtained from the 4 mm DSR test for the unaged, RTFO, 20 hour PAV, 40 hour PAV and 60 hour PAV conditions for the 0%, 5% and 7.5% sterol levels for both the Mayan Crude based Asphalto 64-22 and the Canadian Crude based PG 64-22. The Asphalto 64-22 which exhibited significant decrease in ΔTc with aging was significantly improved with the addition of the sterol additive and again a dose response effect was seen for the Asphalto 64-22 binder although the greatest impact was seen at the 60 hour PAV aged condition. The Canadian Crude based PG 64-22, which does not have a serious problem with negative values of ΔTc also exhibited some improvement in ΔTc with aging, but the effect was much less pronounced.

This comparative analysis of the impact of the sterol additive on asphalt binder binders that exhibit marked differences due to aging suggest that the benefits of the sterol additive are most likely to be of value in asphalt binders that exhibit large decreases in ΔTc with aging.

Figure 8:
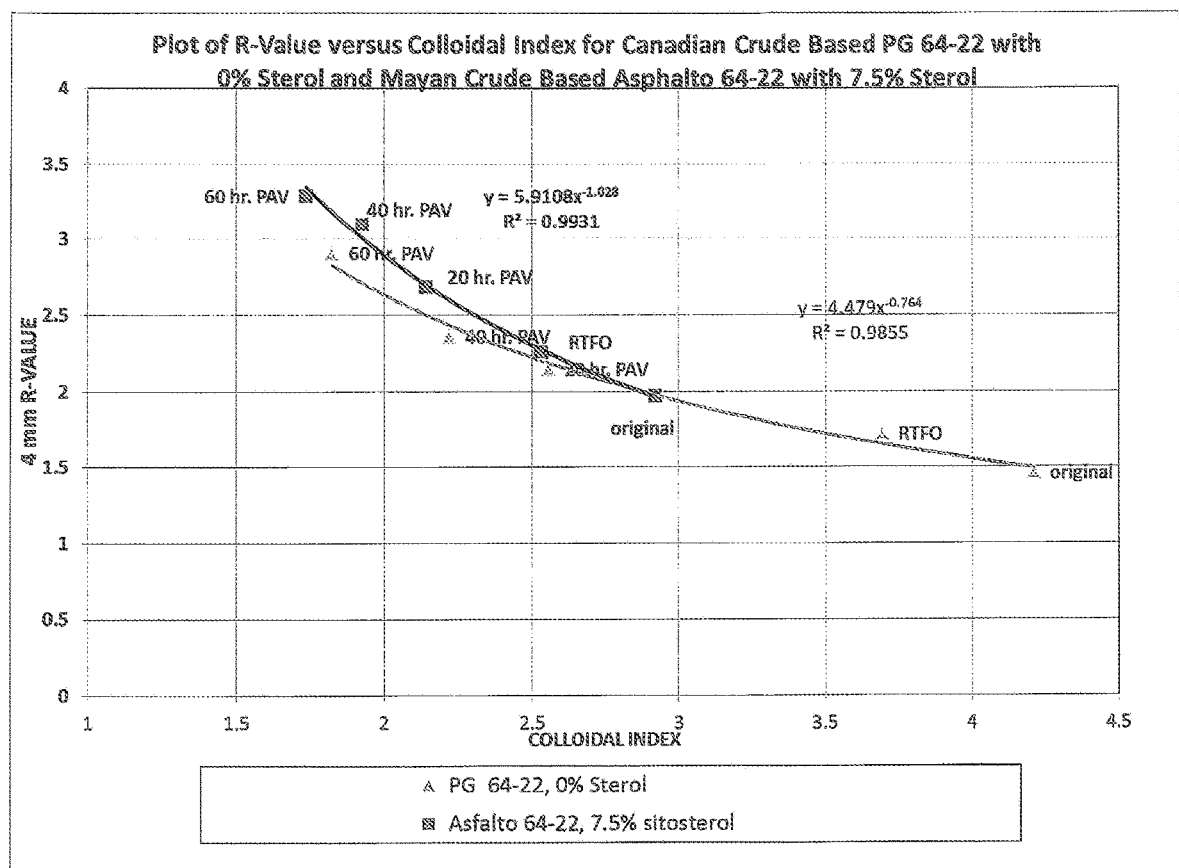
FIG. 8 is a graphical representation of a comparison of R-Value versus Colloidal Index for Canadian crude based PG 64-22 with 0% sterol and Mayan crude based Asphalto 64-22 with 7.5% sterol and both binders aged through 60 hours in the PAV.

FIG. 7 is a plot of R-Value versus Colloidal Index for the Canadian Crude based PG 64-22. The 0% sterol blend showed higher R-Values compared to the 5% and 7.5% blends. However the difference between the sterol blends and the control 0% blend is about half the difference for the Asphalto 64-22. FIG. 8 showed that through a comparison of R-value versus Colloidal Index for the Asphalto 64-22 with 7.5% sterol and the PG 64-22 with no additive that it is possible to move an asphalt binder with severe aging issues closer to the characteristics of an asphalt binder with minimal aging issues.

Example 6

AFM analysis was performed on the samples made with MN1-4, MN1-4+5% Sterol and MN1-4+7.5% Sterol binders in Example 3.

The binders were prepared for AFM by application of a small bead to a steel stub. With a knife, the bead was scraped against the surface of the stub and the resulting film heated to 115° C. for about 2 min to allow the film surface to level. AFM images were captured at room temperature on a Bruker Dimension Icon-PT™ Scanning Probe microscope. Both topographic and friction images were obtained after the asphalt films had been annealed 72 hr. to 96 hr. at room temperature. Antimony doped silicon cantilever tip AFM probes (Bruker Corporation) were used for measurements. Topographic images revealed vertical elevations and declinations associated to surface features, whereas the friction image allowed for differentiation of surface material based on changes in elastic or adhesive properties. The AFM revealed changes in surface composition, without revealing the nature of the change. All the microphotographs show a 20 μm×20 μm region unless otherwise indicated.

Figure 9:
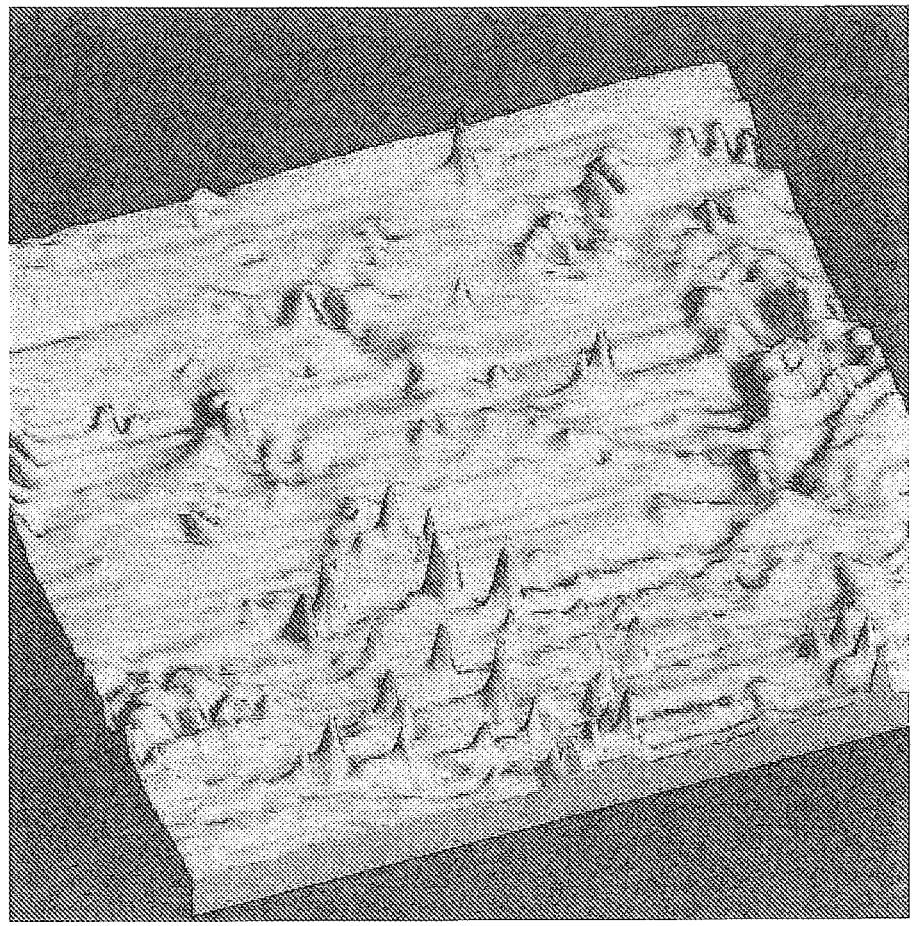
FIG. 9 shows a 3D AFM image of MN1-4 binder with 0% sterol after 60 hours of PAV aging.
Figure 10:
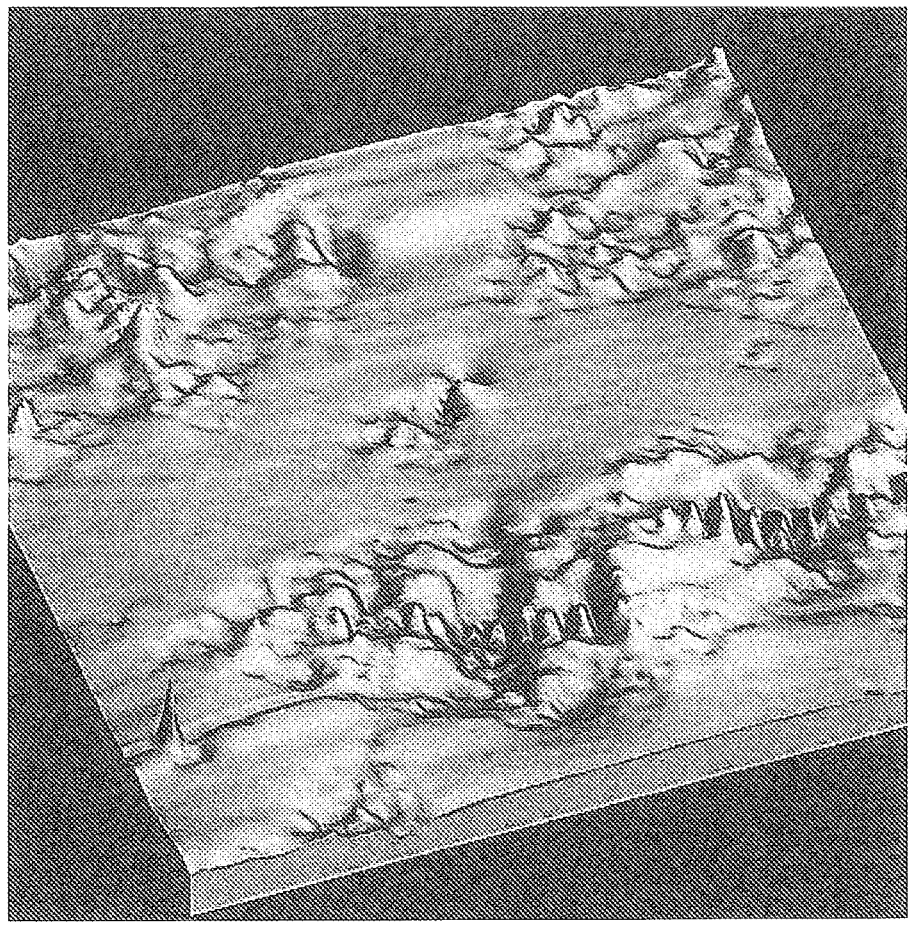
FIG. 10 shows a 3D AFM image of MN1-4 binder with 5% sterol after 60 hours of PAV aging.
Figure 11:
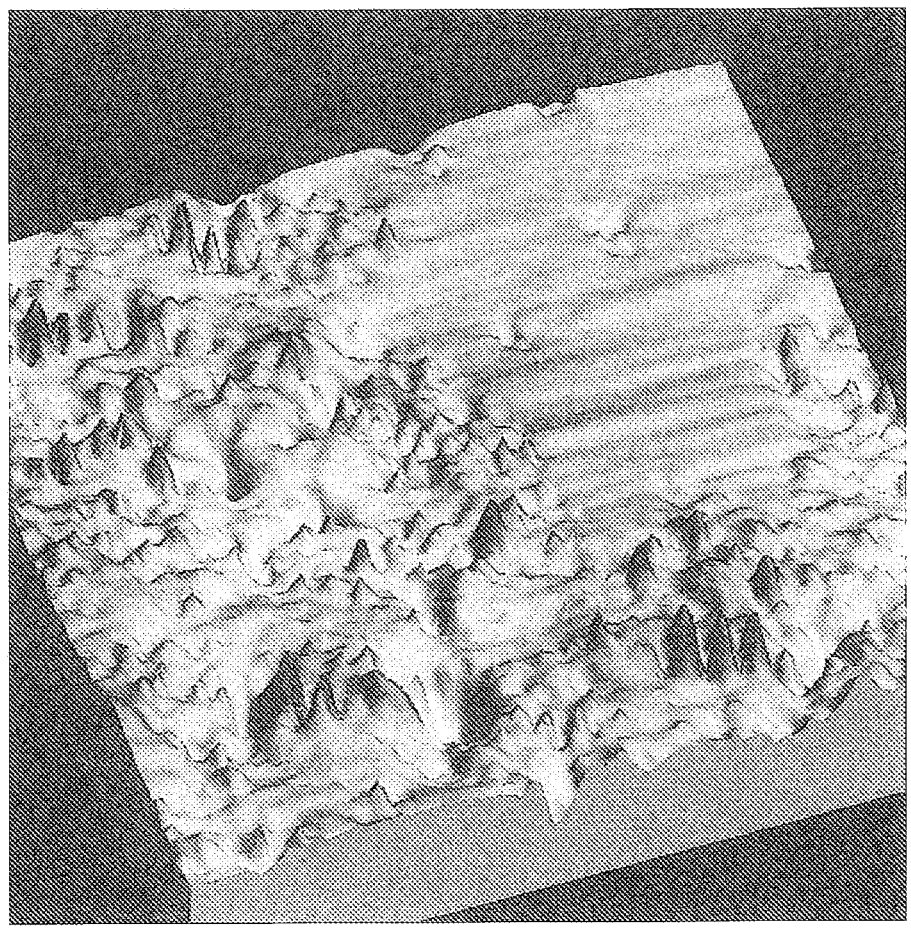
FIG. 11 shows a 3D AFM image of MN1-4 binder with 7.5% sterol after 60 hours of PAV aging.

The AFM data generated was analyzed for surface characteristics and it was discovered that as the binders were aged with increasing levels of sterol, there was an increase in the amount of what we have termed surface defects that developed in the material being imaged. FIGS. 9 (no sterol), 10 (5% sterol), 11 (7.5% sterol) all of which are for 60 hour PAV aged samples, show that the extent to which the surface has become more rough or textured has increased as the images move from 0% to 5% to 7.5% sterol. Table 15 is summary of the surface roughness, expressed as average roughness over the image surface, the average height of the roughness extending out of the surface of the sample, the defect area (i.e. the non-smooth plane of the sample) expressed in μm2 and the defect area expressed as a percent keeping in mind that the area of each image is 400 μm2.

TABLE 13

| Sample | Aging Condition | Colloidal Index | Avg Roughness | Avg Height | Defect area μm² | Defect % | ΔTc | 4 mm_ Rvalue |
|---|---|---|---|---|---|---|---|---|
| MN1-4, 5% Sterol | Unaged | 3.260 | 3.36 | 37.1 | 224.808 | 56.202 | −0.2 | 1.841 |
| MN1-4, 5% Sterol | RTFO | 2.925 | 3.62 | 33 | 266.242 | 66.5605 | −0.5 | 2.043 |
| MN1-4, 5% Sterol | 20 hr. PAV | 2.021 | 5.28 | 33.44 | 204.149 | 51.03725 | −3.3 | 2.499 |
| MN1-4, 5% Sterol | 40 hr. PAV | 1.885 | 11.49 | 78.82 | 181.259 | 45.31475 | −3.8 | 2.742 |
| MN1-4, 5% Sterol | 60 hr. PAV | 2.067 | 8.73 | 72.97 | 222.815 | 55.70375 | −7.0 | 3.051 |
| MN1-4, 7.5% Sterol | Unaged | 3.505 | 109.79 | 413.33 | 400 | 100 | 1.2 | 1.747 |
| MN1-4, 7.5% Sterol | RTFO | 2.953 | 119 | 679.1 | 400 | 100 | −1.0 | 1.928 |
| MN1-4, 7.5% Sterol | 20 hr. PAV | 2.185 | 237.2 | 896.6 | 400 | 100 | −2.9 | 2.274 |
| MN1-4, 7.5% Sterol | 40 hr. PAV | 2.018 | 116 | 663.6 | 214.536 | 53.634 | −3.8 | 2.481 |
| MN1-4, 7.5% Sterol | 60 hr. PAV | 2.125 | 7.46 | 118.342 | 286.273 | 71.56825 | −4.6 | 2.694 |

TABLE 13-continued

| Sample | Aging Condition | Colloidal Index | Avg Roughness | Avg Height | Defect area µm² | Defect % | ΔTc | 4 mm Rvalue |
|---|---|---|---|---|---|---|---|---|
| MN1-4, No Sterol | Unaged | 2.806 | 7.56 | 77.56 | 239.809 | 59.95225 | −1.5 | 2.037 |
| MN1-4, No Sterol | RTFO | 2.581 | 7.033 | 51.81 | 224.281 | 56.07025 | −1.9 | 2.428 |
| MN1-4, No Sterol | 20 hr. PAV | 2.344 | 8.39 | 122.02 | 80.255 | 20.06375 | −4.8 | 2.943 |
| MN1-4, No Sterol | 40 hr. PAV | 2.009 | 4.77 | 90.7 | 79.551 | 19.88775 | −7.6 | 3.062 |
| MN1-4, No Sterol | 60 hr. PAV | 1.890 | 7.58 | 57.96 | 72.963 | 18.24075 | −11.0 | 3.836 |

Figure 12:
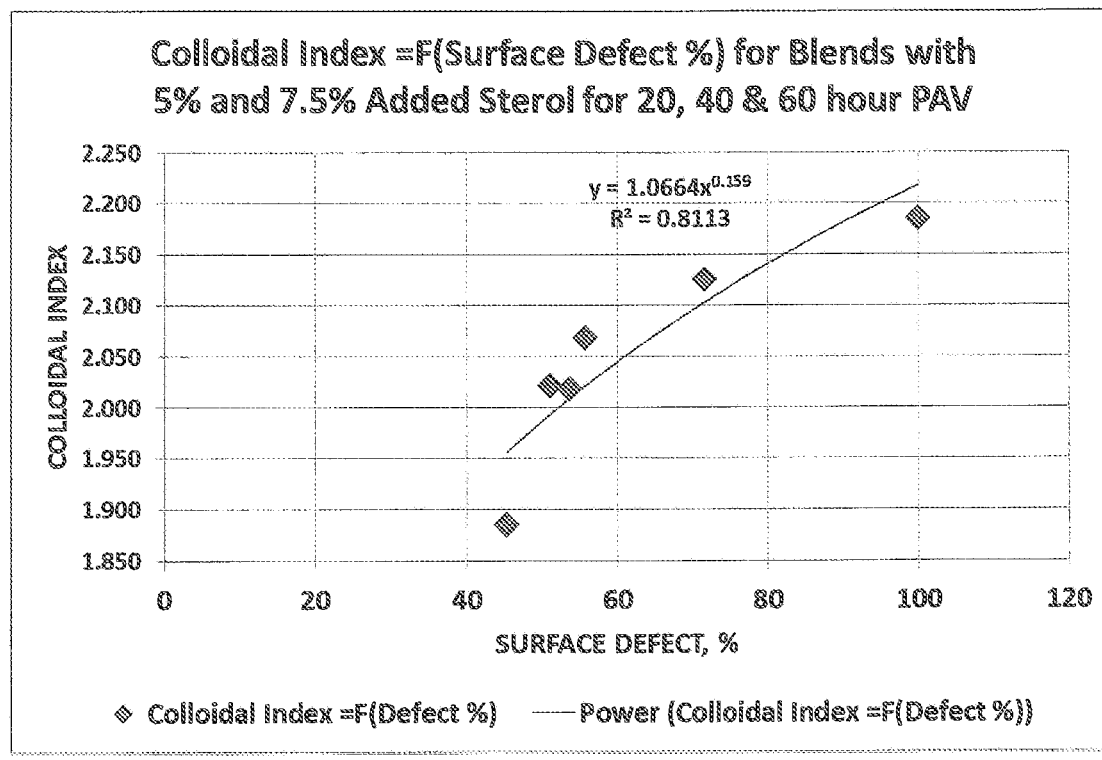
FIG. 12 is a graphical representation of Colloidal Index versus Percent AFM surface defects for 20, 40 and 60 hours of PAV aging for MN-14 binder with 5% and 7.5% sterol.

FIG. 12 is a plot of the Colloidal Index versus the surface defects shown in Table 13 expressed as a percent, for the 5% and 7.5% sterol blend 20, 40 and 60 hour PAV residues. This approach was taken because when all aging conditions were included there was a very poor fit of data which seemed to be related to the small observed change in the Colloidal Index for the unaged and RTFO conditions. By focusing on the impact of the sterol additive after significant aging, a relationship between the chemical compositional changes captured by the Iatroscan test and the changes occurring at the molecular level captured by the AFM became more apparent. As the area occupied by the surface defects decreases, the Colloidal Index also decreases which represents a more aged material. Table 13 shows that as the binders age the general trend is for the defect area to decrease. This is interpreted to mean that initially the components that result in binder degradation are agglomerated and as they age these components oxidize resulting in chemical changes that cause the Colloidal Index to decrease. Namely these changes are an increase in asphaltenes and decrease in cyclics. Also the chemical changes result in reduction in the ability of the binder to relax stresses and this is manifested as increases in R-Value and decreases in ΔTc. As discussed above, the presence of the sterol additive appears to remove those components that cause property degradation and render them less effective than they would otherwise be. As the data shows, this retardation of degradation is not a permanent change in the binder but can substantially extend the time before the binder will reach the state of degradation were the sterol not present.

FIG. 13 shows two plots of R-Value as a function of the Defect area in the AFM images. The diamond symbols are for all the binder aging conditions and the open square symbols are the data with the unaged condition data removed. The curve fit for these data is reasonable showing that as the defect area is reduced, the R-Value increases thus representing a more aged condition. The 20, 40 and 60 hour PAV results for the MN1-4 sample with no sterol are in the upper left quadrant and represent the most aged binder region as the R-Value shows. Also the three least aged 7.5% sterol blends are in the lower right quadrant and represent the least aged condition based on R-Value. In order to provide a less cluttered plot, the unaged sample and unaged control binder data was not included in FIG. 13 plot, as the R-values for the unaged samples were essentially the same as those of the control samples because no oxidation had taken place in these samples.

Figure 14:
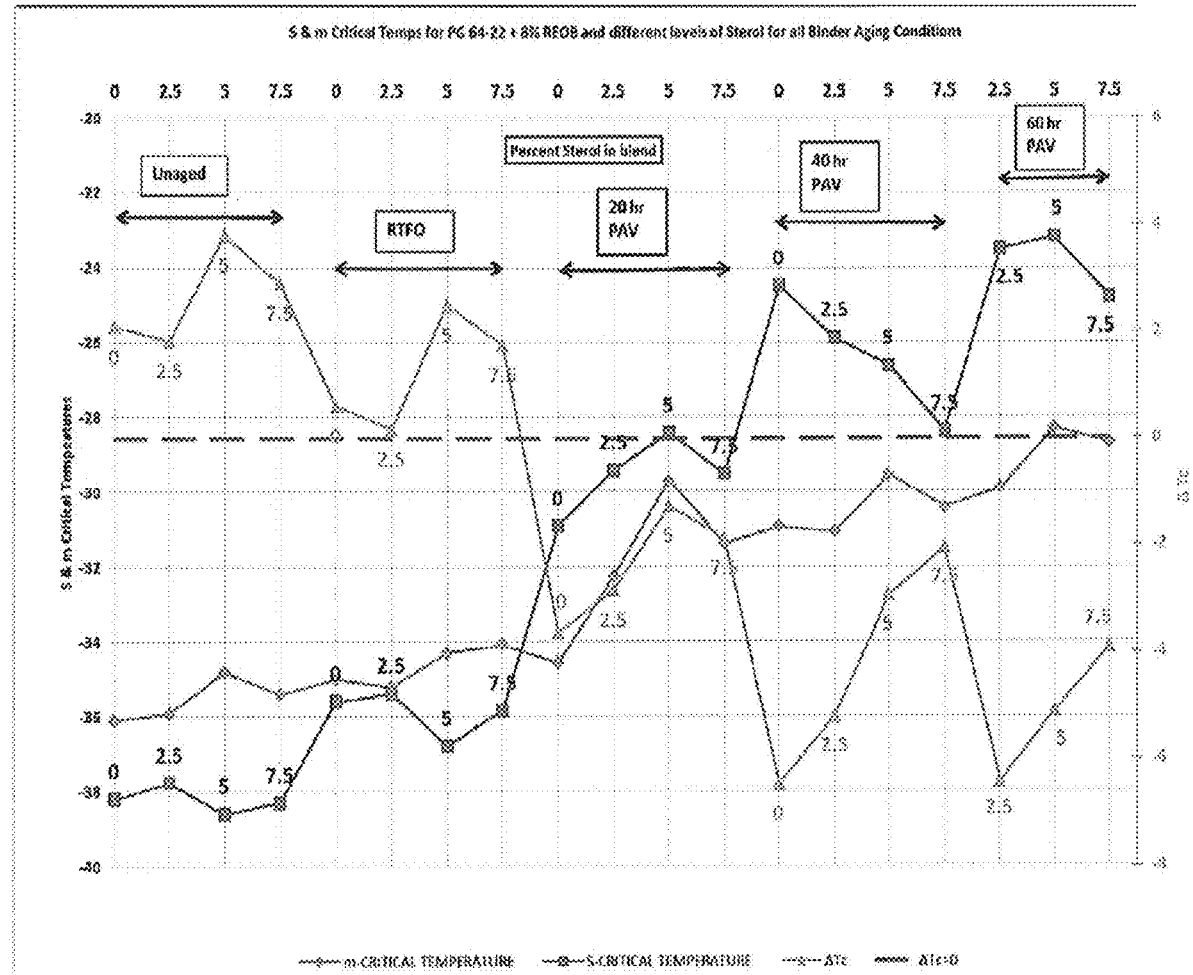
FIG. 14 is a graphical representation of S Critical and m-value Critical temperatures and $\Delta Tc$ for 0%, 2.5%, 5% and 7.5% sterol blends in PG 64-22+8% REOB and aged through 60 hours of PAV aging.

Another interpretation of the data shown in FIG. 14 is that for the 5% sterol blend there is not much change with aging and therefore the 5% addition represents a blend that can be aged through 60 hours with moderate increases in R-Value. The 7.5% sterol addition indicates that in the early stages of aging the sterol actually results in an improvement to the binder by moving the R-Value to a more favorable position (i.e. lower values). For the 7.5% sterol blend it required aging beyond the 20 hour PAV condition to move the R-Value back up to the fitted data line where the 0% and 5% sterol blends began.

Example 7

Sample were made with PG 52-34, no sterol content and 20% binder recovered from post-consumer waste tear-off shingles obtained from Recovery Technology Solutions (RTS), Shakopee, Minn. A similar sample with 5% of the Example 1 mixed sterols (PG 52-34, 5% mixed sterols and 20% binder recovered from post-consumer waste tear-off shingles) was also made using the Example 2 method but with a mixing temperature of 187.8° C.-204° C. (370-400° F.).

The samples with and without sterol were evaluated in as unaged, in a RTFO, or by 20 hours PAV aging and 40 hour PAV aging for low temperature stiffness critical temperature (TSCrit) and low temperature m-value critical temperature (Tm-Crit) at each aged condition using the above-mentioned 4 mm DSR test method. The ΔTc parameter was also calculated. The more negative the ΔTc parameter, the less the binder was able to relax stresses and the more prone to fatigue cracking the mixture containing the binder became.

The data shown in Table 14 summarizes the low temperature data measured and the ΔTc results calculated from the measured data.

TABLE 14

| Binder | Shingle binder from tear-off shingles | Aging | $T_{SCrit}$ Grade | $T_{m\text{-}Crit}$ Grade | ΔTc |
|---|---|---|---|---|---|
| PG 52-34, no Sterol | 20% | Unaged | −36.2 | −39.8 | 3.6 |
| PG 52-34, no Sterol | 20% | RTFO | −37 | −38.2 | 1.2 |
| PG 52-34, no Sterol | 20% | 20 hr. PAV | −34.7 | −33.1 | −1.6 |

TABLE 14-continued

| Binder | Shingle binder from tear-off shingles | Aging | $T_{SCrit}$ Critical Grade | $T_{m\text{-}Crit}$ Grade | ΔTc |
|---|---|---|---|---|---|
| PG 52-34, no Sterol | 20% | 40 hr. PAV | −34.3 | −29.6 | −4.6 |
| PG 52-34 + 5% Sterol | 20% | Unaged | −37.4 | −40.8 | 3.4 |
| PG 52-34 + 5% Sterol | 20% | RTFO | −36.6 | −39.5 | 2.9 |
| PG 52-34 + 5% Sterol | 20% | 20 hr. PAV | −32.8 | −34 | 1.2 |
| PG 52-34 + 5% Sterol | 20% | 40 hr. PAV | −33.5 | −31.6 | −1.9 |

It can be seen in Table 14 that although both binder samples begin with similar ΔTc values, as the binders were aged, they became increasingly more negative for the samples with no sterol relative to the samples with the 5% sterol. At the 40 hour PAV aged condition, the ΔTc value for the sterol blend was 58% greater than the 40 hour PAV ΔTc value for the samples without sterol.

A second series of samples (Blend #2) was produced and evaluated as described above. Blend #2 used a PG 58-28 binder with no sterol and was blended with 10% binder recovered from post-consumer waste tear-off shingles. The same PG 58-28 binder was also combined with 7.5% of the Example 1 mixed sterols blended with 20% post-consumer waste tear-off shingles. Samples with and without sterol were aged through the 40 hour PAV condition. The data shown in Table 15 summarizes the results of those tests.

TABLE 15

| Binder | Shingle binder from tear-off shingles | Aging | $T_{SCrit}$ Grade | $T_{m\text{-}Crit}$ Grade | ΔTc |
|---|---|---|---|---|---|
| PG 58-28, no sterol | 10% | Unaged | −34.3 | −36.7 | 2.4 |
| PG 58-28, no sterol | 10% | RTFO | −32.2 | −33.1 | 0.9 |
| PG 58-28, no sterol | 10% | 20 hr. PAV | −31.7 | −30.5 | −1.2 |
| PG 58-28, no sterol | 10% | 40 hr. PAV | −30 | −26 | −4.1 |
| PG 58-28, 7.5% sterol | 20% | Unaged | −33.5 | −36.1 | 2.6 |
| PG 58-28, 7.5% sterol | 20% | RTFO | −32.7 | −35.6 | 2.9 |
| PG 58-28, 7.5% sterol | 20% | 20 hr. PAV | −29.7 | −31 | 1.3 |
| PG 58-28, 7.5% sterol | 20% | 40 hr. PAV | −27.5 | −26.4 | −1 |

The data in Table 15 shows that even though the no sterol blend contained only half as much recovered shingle binder, the 7.5% sterol/20% shingle binder blend had similar S Critical values and that the even more important m-value Critical grades were nearly identical to those of the no sterol. The 20% shingle binder with 7.5% sterol thus had a ΔTc value after 40 hours of PAV aging that was only −1° C. compared to −4.1° C. for the 10% shingle binder with no sterol. In effect the addition of 7.5% sterol enables twice as much shingle binder to be used with this PG 58-28 while still obtaining a better overall performance binder than the 10% shingle binder with no sterol.

Example 8

To further evaluate whether the use of mixed sterols could mitigate the excessive ΔTc results observed with REOB in binders, four samples with varying amount of sterol were evaluated. The samples were produced as in Example 2. The REOB s require less heat compared to the blends with recovered shingle binder as in Example 1. The mixed sterols used were the same as those described in Example 1.

Using PG64-22 binder, samples were produced using 0%, 2.5%, 5% and 7.5% mixed sterols with 8% REOB and tested for their low temperature stiffness and m-value critical temperatures in the unaged, RTFO aged, 20 hour PAV aged, 40 hour PAV and 60 hour PAV conditions using the 4 mm DSR test procedure.

The data is shown in Table 16 and plotted in FIG. 14.

TABLE 16

| Sample description | Binder Aging | % Sterol | % REOB | S_critical | m_critical | ΔTc |
|---|---|---|---|---|---|---|
| RHEA G(t) @ −24° C. 1531, 06-03-15-G, MIA 64-22 (Tk 6 Winter Fill), 8% REOB, Unaged, 4 mm, HR3-2, HR3-2 | unaged | 0 | 8 | −36.1 | −38.2 | 2.1 |
| RHEA G(t) @ −24° C. 1531, 06-09-15-G, MIA 64-22, 8% Saftey Kleen, 2.5% Plant Sterols Unaged, 4 mm, HR3-2-2 | unaged | 2.5 | 8 | −35.9 | −37.8 | 1.8 |
| G(t) @ −30° C. 1531, RHEA G(t) @ −24° C. 1531, 05-28-15-B, MIA 64-22 (Tk 6), 8% REOB, 5% Plant Sterols, Unaged, 4 mm, HR3-4 | unaged | 5 | 8 | −34.8 | −38.6 | 3.8 |
| RHEA G(t) @ −24° C. 1531, 05-28-15-C, MIA 64-22 (Tk 6 ) | unaged | 7.5 | 8 | −35.4 | −38.3 | 2.9 |

TABLE 16-continued

| Sample description | Binder Aging | % Sterol | % REOB | S_critical | m_critical | ΔTc |
|---|---|---|---|---|---|---|
| 8% REOB, 7.5% Plant Sterols, Unaged, 4 mm, HR3-2 | | | | | | |
| RHEA G(t) @ −24° C. 1531, 06-03-15-G, MIA 64-22 (Tk 6 Winter Fill), 8% REOB, RTFO, 4 mm, HR3-2, HR3-2 | RTFO | 0 | 8 | −35.0 | −35.6 | 0.6 |
| RHEA G(t) @ −24° C. 1531, 06-09-15-G, MIA 64-22, 8% Saftey Kleen, 2.5% Plant Sterols, RTFO, 4 mm, HR3-2 | RTFO | 2.5 | 8 | −35.2 | −35.4 | 0.2 |
| G(t) @ −30° C. 1531, RHEA G(t) @ −24° C. 1531, 05-28-15-B, MIA 64-22 (Tk 6), 8% REOB, 5% Plant Sterols, RTFO 4 mm, HR3-4 | RTFO | 5 | 8 | −34.3 | −36.8 | 2.5 |
| RHEA G(t) @ −24° C. 1531, 05-28-15-C, MIA 64-22 (Tk 6), 8% REOB, 7.5% Plant Sterols, RTFO, 4 mm, HR3-2 | RTFO | 7.5 | 8 | −34.1 | −35.8 | 1.8 |
| RHEA G(t) @ −24° C. 1531, 06-03-15-G, MIA 64-22 (Tk 6 Winter Fill), 8% REOB, 20 hr. PAV, 4 mm, HR3-2, HR3-2 | 20 hr. PAV | 0 | 8 | −34.6 | −30.9 | −3.6 |
| RHEA G(t) @ −24° C. 1531, 06-09-15-G, MIA 64-22, 8% Saftey Kleen, 2.5% Plant Sterols 20 hr. PAV, 4 mm, HR3-2-2 | 20 hr. PAV | 2.5 | 8 | −32.3 | −29.4 | −2.8 |
| G(t) @ −30° C. 1531, RHEA G(t) @ −24° C. 1531, 05-28-15-B, MIA 64-22 (Tk 6), 8% REOB, 5% Plant Sterols, 20 hr. PAV, 4 mm, HR3-4 | 20 hr. PAV | 5 | 8 | −29.7 | −28.4 | −1.3 |
| RHEA G(t) @ −24° C. 1531, 05-28-15-C, MIA 64-22 (Tk 6), 8% REOB, 7.5% Plant Sterols, 20 hr. PAV, 4 mm, HR3-2 | 20 hr. PAV | 7.5 | 8 | −31.4 | −29.5 | −1.9 |
| RHEA G(t) @ −24° C. 1531, 06-03-15-G, MIA 64-22, (Tk 6 Winter Fill), 8% REOB, Unaged, 4 mm, HR3-2, HR3-2 | 40 hr. PAV | 0 | 8 | −30.9 | −24.5 | −6.5 |
| RHEA G(t) @ −24° C. 1531, 06-09-15-G, MIA 64-22, 8% Saftey Kleen, 2.5% Plant Sterols 40 hr. PAV, 4 mm, HR3-2-2 | 40 hr. PAV | 2.5 | 8 | −31.1 | −25.9 | −5.2 |
| G(t) @ −30° C. 1531, RHEA G(t) @ −24° C. 1531, 05-28-15-B, MIA 64-22 (Tk 6), 8% REOB, 5% Plant Sterols, 40 hr. PAV, 4 mm, HR3-4 | 40 hr. PAV | 5 | 8 | −29.6 | −26.6 | −2.9 |
| RHEA G(t) @ −24° C. 1531, 05-28-15-C, MIA 64-22, (Tk 6), 8% REOB, 7.5% Plant Sterols, Unaged, 4 mm, HR3-2 | 40 hr. PAV | 7.5 | 8 | −30.4 | −28.4 | −2.0 |
| RHEA G(t) @ −24° C. 1531, 06-09-15-G, MIA | 60 hr. PAV | 2.5 | 8 | −29.9 | −23.5 | −6.4 |

TABLE 16-continued

| Sample description | Binder Aging | % Sterol | % REOB | S_critical | m_critical | ΔTc |
|---|---|---|---|---|---|---|
| 64-22, 8% Saftey Kleen, 2.5% Plant Sterols, 60 hr. PAV, 4 mm, HR3-2-2 G(t) @ −30° C. 1531, RHEA G(t) @ −24° C. 1531, 05-28-15-B, MIA 64-22 (Tk 6), 8% REOB, 5% Plant Sterols, 60 hr. PAV, 4 mm, HR3-4 | 60 hr. PAV | 5 | 8 | −28.3 | −23.2 | −5.1 |
| RHEA G(t) @ −24° C. 1531, 05-28-15-C, MIA 64-22 (Tk 6), 8% REOB, 7.5% Plant Sterols, 60 hr. PAV, 4 mm, HR3-2 | 60 hr. PAV | 7.5 | 8 | −28.7 | −24.8 | −3.9 |

The data shows that for all samples the stiffness and m-value critical temperatures increase with each aging condition and the ΔTc decreases for each aging condition. In general, for this binder and this amount of REOB, the 2.5% sterol blend is not as effective as the 5% or 7.5% sterol blends, but the 2.5% sterol blend yields results superior to the blend that contains 0% sterol at all aging conditions. The data also shows that the m-value critical temperature increases at a faster rate than does the stiffness critical temperature. That demonstrates that the presence of the REOB impacts the ability of the binder to relax stresses in a negative manner, but also shows that the presence of the sterol additive retards the impact of the REOB on the increase in the m-value. At the 40 hour PAV condition, the m-value for the 7.5% sterol blend is 3.9° C. lower than the 0% blend and the 5% Sterol blend is 2.1° C. lower than the 0% blend. The data also shows that the ΔTc for the 5% and 7.5% blends at 40 hours of PAV aging is less negative (superior) to the ΔTc of the 0% sterol blend at 20 hours of PAV aging. Similarly the ΔTc for the 5% and 7.5% blends at 60 hours of PAV aging is less negative (superior) to the ΔTc of the 0% sterol blend at 40 hours of PAV aging. The ΔTc for the 60 hour 7.5% sterol blend PAV residue is comparable to the ΔTc for the 20 hour 0% sterol blend PAV residue. Further the ΔTc for the 60 hour 5% sterol blend PAV residue is comparable to the ΔTc for the 40 hour 2.5% sterol blend PAV residue, and the ΔTc for the 60 hour 2.5% sterol blend PAV residue is comparable to the ΔTc for the 40 hour 0% sterol blend PAV residue. These data comparisons show that even a low dosage level of the sterol additive improves the aging behavior of the PG 64-22 plus 8% REOB blended binder relative to the control sample with no sterol additive. These data also show there is a definite dose response improvement to the retardation of aging. For this particular PG 64-22 binder blended with 8% REOB, the 7.5% sterol addition would based on the ΔTc parameter enable the binder to be aged three times longer than the untreated binder before a similar aging impact would be observed. The 5% sterol addition would based on the ΔTc parameter enable the binder to be aged approximately 2.5 times longer than the untreated binder.

Some additional non-limiting embodiments are provided below to further exemplify the present disclosure:

1. An asphalt paving comprising aggregate, virgin asphalt binder, reclaimed asphalt binder material comprising RAP, RAS or combinations of both, a triterpenoid, and a softening agent, wherein the triterpenoid is free of cyclic organic compositions that contain esters or ester blends, and has a sterol content of about 0.5 to about 15 wt. % of the virgin asphalt binder.

2. An asphalt binder comprising virgin asphalt binder, reclaimed asphalt binder material comprising RAP, RAS or combinations of both, a triterpenoid, and a softening agent, wherein the triterpenoid is free of cyclic organic compositions that contain esters or ester blends, and has a sterol content of about 0.5 to 15 about wt. % of the virgin asphalt binder.

3. A method for retarding oxidative aging of an asphalt binder, which method comprises adding one of more triterpenoid or a triterpenoid blend to a bituminous or asphalt binder, wherein the triterpenoid or triterpenoid blend does not contain an ester or an ester blend, and wherein the triterpenoid or triterpenoid blend is about 0.5 to 15 wt. % of the asphalt binder weight and about 1 to about 10 wt. %, or about 1 to about 3 wt. % of the asphalt binder weight.

4. A method for reusing reclaimed asphalt binder for asphalt pavement production, which method comprises adding to the reclaimed binder about 0.5 to about 15 wt. %., about 1 to about 10 wt. %., or about 1 to about 3 wt. % of a triterpenoid or a triterpenoid blend that does not contain an ester or an ester blend.

5. A method for applying a road pavement surface which method comprises preparing, mixing, applying to a base surface and compacting an asphalt binder paving of embodiment 1.

6. A composition or method of any of the preceding embodiments wherein the triterpenoid is a sterol.

7. A composition or method of any of the preceding embodiments wherein the triterpenoid is a stanol.

8. A composition or method of any of the preceding embodiments wherein the triterpenoid is a plant sterol.

9. A composition or method of any of the preceding embodiments wherein the triterpenoid is a plant stanol.

10. A composition or method of any of the preceding embodiments wherein the reclaimed asphalt binder material is or comprises RAP.

11. A composition or method of any of the preceding embodiments wherein the reclaimed asphalt binder material is or comprises RAS.

12. A composition or method of any of the preceding embodiments wherein the triterpenoid content is about 1 to about 15 wt. % of the asphalt binder weight.

13. A composition or method of any of the preceding embodiments wherein the asphalt binder composition comprises RAS at a binder replacement level 1% or greater.

14. A composition or method of any of the preceding embodiments wherein the asphalt binder composition comprises RAP at a binder replacement level 10% and greater or 20% and greater.

15. A composition or method of any of the preceding embodiments wherein the asphalt binder composition comprises RAP and RAS used in combination at a RAP binder replacement level of 10% and greater and a RAS binder replacement level of 1% and greater.
16. A composition or method of any of the preceding embodiments wherein the asphalt binder composition comprises asphalt binder extracted and recovered from post-consumer waste shingles at levels of 1% by weight and greater or 5% by weight and greater.
17. A composition or method of any of the preceding embodiments wherein the asphalt binder composition comprises asphalt binder extracted from manufacture's waste shingles at levels of 1% by weight and greater, 2% by weight and greater or 5% by weight and greater.
18. A composition or method of any of the preceding embodiments wherein the asphalt binder composition comprise oxidized asphalt binders meeting ASTM specification D312 for Type II, Type III, Type IV and coating asphalt binder at levels of 1% by weight and greater or 5% by weight and greater.
19. A composition or method of any of the preceding embodiments wherein the asphalt binder composition comprises extracted and recovered RAP at levels of 10% by weight and greater.
20. A composition or method of any of the preceding embodiments wherein the asphalt binder composition comprises re-refined engine oil bottoms at levels of 1% and greater or 3% and greater by weight or volume percent.
21. A composition or method of any of the preceding embodiments wherein the asphalt binder composition comprises paraffinic oils at levels of 1% and greater by weight or volume percent.

Further additional non-limiting embodiments are provided below to further exemplify the present disclosure:

1. An asphalt binder comprising virgin asphalt binder, reclaimed asphalt binder material comprising RAP, RAS or combinations of both and 0.5 to 15 wt. % of an anti-aging additive based on the virgin asphalt binder.
2. The asphalt binder of embodiment 1, wherein the anti-aging additive is 1 wt. % to 10 wt. %, or 1 wt. % to 3 wt. % of the virgin asphalt binder.
3. The asphalt binder of embodiment 1, wherein the anti-aging additive comprises a triterpenoid or triterpenoid blend.
4. The asphalt binder of embodiment 3, wherein the triterpenoid comprises a sterol.
5. The asphalt binder of embodiment 3, wherein the triterpenoid comprises a stanol.
6. The asphalt binder of embodiment 4, wherein the sterol comprises a plant sterol.
7. The asphalt binder of embodiment 5, wherein the stanol comprises a plant stanol.
8. The asphalt binder of embodiment 1, further comprising a softening agent.
9. The asphalt binder of embodiment 8, wherein the softening agent comprises a re-refined engine oil bottoms.
10. The asphalt binder of embodiment 1, further comprising aggregate.
11. The asphalt binder of embodiment 1, wherein the asphalt binder provides a ΔTc of −5.0 or greater.
12. The asphalt binder of embodiment 1, wherein the anti-aging additive is present in an amount effective to provide a less negative ΔTc value after aging the asphalt binder compared to a similarly-aged binder without the anti-aging additive.
13. A paved surface comprising the asphalt binder of embodiment 1.
14. A method for slowing the aging or restoring aged asphalt binder comprising:
    adding an anti-aging additive to an asphalt binder, wherein the asphalt binder comprises a virgin asphalt binder, reclaimed asphalt binder material comprising RAP, RAS or combinations of both and 0.5 wt. % to 15 wt. % of an anti-aging additive based on the virgin asphalt binder.
15. The method of embodiment 14, wherein the anti-aging additive is 1 wt. % to 10 wt. %, or 1 wt. % to 3 wt. % of the virgin asphalt binder.
16. The method of embodiment 14, wherein the anti-aging additive comprises a triterpenoid.
17. The method of embodiment 16, wherein the triterpenoid comprises a sterol.
18. The method of embodiment 16, wherein the triterpenoid comprises a stanol.
19. The method of embodiment 17, wherein the sterol comprises a plant sterol.
20. The method of embodiment 18, wherein the stanol comprises a plant stanol.
21. A method to identity at least one deleterious component present in an asphalt binder comprising measuring defect areas in an Atomic Force Microscopy image.
22. The method according to embodiment 21, wherein the deleterious component is a waste engine oil or a Re-refined Engine Oil Bottoms.
23. The method according to embodiment 21, wherein the deleterious component is Vacuum Tower Asphalt Extender.
24. The method according to embodiment 21, wherein the deleterious component is any drain oil product or waste engine oil material with or without post-consumer processing.
25. The method according to embodiment 21, wherein the deleterious component is paraffinic processing oil.
26. The method according to embodiment 21, wherein the deleterious component is lubricating base oil.
27. The method according to claim 21, wherein the deleterious component is asphalt binder extracted from a paving mixture containing RAP and the RAP is present in an asphalt binder in an amount ranging from 0.1% to 100% of the paving mixture.
28. The method according to claim 21, wherein the deleterious Component is asphalt binder extracted from a paving mixture containing RAS and the RAS is present in a binder replacement amount of 0.1% to 50%.
29. The method according to embodiment 21, wherein the deleterious material is asphalt binder extracted from a paving mixture containing RAP and RAS, and wherein a combination of RAP and RAS is present in an asphalt binder in an amount of 0.1% to 100%.
30. The method according to embodiment 21, wherein deleterious material is naturally occurring in an asphalt binder and not resulting from any materials added after the asphalt binder has been produced.
31. A method of using Atomic Force Microscopy comprising identity asphalt binders with high levels of defect areas as it ages which are associated with deleterious asphalt binder components.
32. A method of using Atomic Force Microscopy comprising screening additives suitable for preventing deleterious binder components from causing high levels of defect areas in bulk asphalt binder as it ages.
33. The method according to embodiments 31 or 32, wherein aging is un-accelerated aging, Rolling Thin Film Oven aging (RTFO aged), 20 hours of PAV aging, 40 hours of PAV aging, additional multiples of 20 hours of PAV aging after 40 hours of PAV aging.
34. The method according to embodiment 33, wherein amounts of defect areas in the asphalt binder are determined after multiple aging conditions.
35. A method of using Atomic Force Microscopy to identity at least one deleterious component present in an aged asphalt binder sample comprising measuring defect areas in an Atomic Force Microscopy image.
36. The method according embodiment 35, wherein the aged asphalt binder sample is extracted from the upper ½ inch of a pavement sample obtained from a road
37. The method according embodiment 35, wherein the aged asphalt binder sample is a pavement sample has been in place from 1 day to 10 years inclusive.
38. The method according embodiment 35, wherein the aged asphalt binder is extracted from any depth of a pavement layer including the full pavement layer.
39. The method according embodiment 35, wherein the aged asphalt binder sample is taken from a freshly product bituminous mixture prior to paving.
40. An asphalt binder comprising 1 to 10 wt % triterpenoids and 1 to 8% wt % bio-derived or petroleum-derived oil based on total asphalt binder weight.
41. The asphalt binder of embodiment 40, wherein the asphalt binder is a Performance Graded binder with or without polymer modification
42. The asphalt binder of embodiment 40, wherein the asphalt binder contains 0.1 to 2 wt % polyphosphoric acid based on total asphalt binder weight.
43. The asphalt binder of embodiment 40, wherein the asphalt binder containing the sterol and bio-derived or petroleum-derived oil is blended with recovered asphalt from tear off shingles or manufacturer's waste shingles.
44. The asphalt binder of embodiment 43, wherein the shingles are tear off shingles.
45. The asphalt binder of embodiment 43, wherein the shingles are from manufacturer's waste shingles.
46. The asphalt binder of embodiment 40, wherein the asphalt binder containing the sterol and bio-derived or petroleum-derived oil is used to produce a paving mixture containing 10 to 70 wt % RAP based on weight of the paving mixture
47. The asphalt binder of embodiment 40, wherein the asphalt binder containing the sterol and bio derived or petroleum derived oil is used to produce a paving mixture containing 1 to 7 wt % RAS based on weight of the paving mixture.

The invention claimed is:

1. A method for identifying the extent of aging in an aged asphalt binder and slowing the aging of the aged asphalt binder comprising:
analyzing the aged asphalt binder for surface defects using atomic force microscopy; and
adding amounts of an anti-aging additive comprising sterol or stanol and a virgin asphalt binder to the aged asphalt binder, wherein the anti-aging additive slows the aging rate of the asphalt binder composition compared to an asphalt binder composition without the age-retarding additive.

2. The method according to claim 1, wherein the asphalt binder is derived from asphalt comprising re-refined engine oil bottoms or vacuum tower asphalt extender.
3. The method according to claim 1, wherein the asphalt binder is derived from asphalt comprising drain oil product or waste engine oil material with or without post-consumer processing.
4. The method according to claim 1, wherein the asphalt binder is derived from asphalt comprising paraffinic processing oil.
5. The method according to claim 1, wherein the asphalt binder is derived from asphalt comprising lubricating base oil.
6. The method according to claim 1, wherein the asphalt binder is derived from a paving mixture containing reclaimed asphalt pavement (RAP) and the RAP is present in an amount of 0.1% to 100% of the asphalt binder weight.
7. The method according to claim 1, wherein the asphalt binder is derived from a paving mixture containing reclaimed asphalt shingles (RAS) and the RAS is present in binder in an amount of 0.1% to 50% of the total asphalt binder weight.
8. The method according to claim 1, wherein the asphalt binder is derived from a paving mixture containing RAP and RAS, and wherein a combination of RAP and RAS is present in an amount of 0.1% to 100% of the total binder weight.
9. The method according to claim 1, wherein the asphalt binder is derived from the upper 13 mm (½ inch) of a pavement sample obtained from a road.
10. The method according to claim 1, wherein the asphalt binder is derived from a pavement sample aged in place from 1 day to 10 years.
11. The method according to claim 1, wherein the asphalt binder is derived from any depth of a pavement layer including a full pavement layer.
12. The method according to claim 1, wherein the asphalt binder comprises a virgin asphalt binder prior to paving.
13. The method according to claim 1, wherein the anti-aging additive comprises 0.5 to 15 wt. % of the anti-aging additive based on the virgin asphalt binder weight.
14. The method according to claim 1, wherein the sterol or stanol comprises a plant sterol or plant stanol.
15. The method according to claim 1, wherein the anti-aging additive is present in an amount effective to provide a decreased R value after aging the asphalt binder compared to the similarly-aged asphalt binder without the anti-aging additive.
16. The method according to claim 1, wherein the anti-aging additive is present in an amount effective to provide a less negative ΔTc value after aging the asphalt binder compared to the similarly-aged asphalt binder without the anti-aging additive.
17. The method according to claim 1, wherein the anti-aging additive is present in an amount effective to provide a ΔTc of greater than or equal to −5.0° C.
18. The method according to claim 1, wherein the asphalt binder is derived from a pavement aged for more than five years.
19. The method according to claim 1, wherein the sterol or stanol is derived from a tall oil pitch.
20. The method according to claim 1, wherein the sterol or stanol is derived from soybean oil or corn oil.

* * * * *

UNITED STATES PATENT AND TRADEMARK OFFICE
CERTIFICATE OF CORRECTION

PATENT NO. : 11,168,214 B2  
APPLICATION NO. : 16/308367  
DATED : November 9, 2021  
INVENTOR(S) : Gerald H. Reinke, Gaylon L. Baumgardner and Andrew Hanz Page 1 of 1

It is certified that error appears in the above-identified patent and that said Letters Patent is hereby corrected as shown below:

On the Title Page

(73) Assignees:
Ergon Asphalt & Emulsions, Inc., "Lackson" should be --Jackson--.

Signed and Sealed this
Fifth Day of July, 2022

Katherine Kelly Vidal
*Director of the United States Patent and Trademark Office*